the patent is extended or adjusted under 35
U.S.C. 154(b) by 0 days.

(12) United States Patent
Kadowaki et al.

(10) Patent No.: US 7,723,569 B2
(45) Date of Patent: May 25, 2010

(54) METHOD FOR PRODUCING UBIQUINONE-10 IN PLANT

(75) Inventors: Koichi Kadowaki, Tsukuba (JP); Sakiko Takahashi, Tsukuba (JP); Makoto Kawamukai, Matsue (JP); Hiroaki Shimada, Tokyo (JP)

(73) Assignees: National Institute of Agrobiological Sciences, Ibaraki (JP); National University Corporation Shimane University, Shimane (JP); Tokyo University of Science, Tokyo (JP)

( * ) Notice: Subject to any disclaimer, the term of this patent is extended or adjusted under 35 U.S.C. 154(b) by 0 days.

(21) Appl. No.: 11/119,351

(22) Filed: Apr. 29, 2005

(65) Prior Publication Data
US 2006/0010519 A1 Jan. 12, 2006

(30) Foreign Application Priority Data

Apr. 30, 2004 (JP) ............................ 2004-136906
Jan. 5, 2005 (JP) ............................ 2005-000984

(51) Int. Cl.
*C12N 15/82* (2006.01)
*C12N 15/11* (2006.01)
*C12N 15/31* (2006.01)
*A01H 5/00* (2006.01)
*A01H 5/10* (2006.01)

(52) U.S. Cl. ............... 800/288; 800/278; 800/295; 800/298; 435/320.1; 435/468; 536/23.1; 536/23.7

(58) Field of Classification Search ............... None
See application file for complete search history.

(56) References Cited

U.S. PATENT DOCUMENTS

2003/0033626 A1 * 2/2003 Hahn et al. ............. 800/278

OTHER PUBLICATIONS

Memelink 2005 Current Opinion in Plant Biology 8:230-235.*
Okada et al 1998 Eur. J. Biochem. 255:52-59, and GenBank Accession AB006850.*
Kubo et al 1999 Proc. Natl. Acad. Sci. 96:9207-9211 and GenBank Accession AB017427.*
Fischer et al 2000 Transgenic Research 9:279-299.*

* cited by examiner

*Primary Examiner*—Anne Marie Grunberg
*Assistant Examiner*—Brent Page
(74) *Attorney, Agent, or Firm*—King & Spalding LLP; Susan J. Myers Fitch; Peter J. Dehlinger

(57) ABSTRACT

A plant which expresses a large amount of ubiquinone-10 and a method for producing ubiquinone-10 using the plant are provided. A dietary supplement, a food and a food additive which contains ubiquinone-10 produced by the plant or the method are provided. The plant is produced by transformation using an expression cassette in which a decaprenyl diphosphate synthase gene is operatively linked with a mitochondrial targeting sequence.

14 Claims, 11 Drawing Sheets

| | | | | | | | | | | | | | | | | |
|---|---|---|---|---|---|---|---|---|---|---|---|---|---|---|---|---|
| atg | gcc | gcc | aag | ata | cgc | ata | gtg | atg | aaa | tct | ttt | atg | agc | caa | gct | 48 |
| Met | Ala | Ala | Lys | Ile | Arg | Ile | Val | Met | Lys | Ser | Phe | Met | Ser | Gln | Ala | |
| 1 | | | | 5 | | | | | 10 | | | | | 15 | | |
| | | | | | | | | | | | | | | | | |
| aac | aaa | gtt | gaa | ggg | gtt | att | cca | tac | gcg | cag | aag | gtt | gga | ttg | cct | 96 |
| Asn | Lys | Val | Glu | Gly | Val | Ile | Pro | Tyr | Ala | Gln | Lys | Val | Gly | Leu | Pro | |
| | | | 20 | | | | | 25 | | | | | 30 | | | |
| | | | | | | | | | | | | | | | | |
| gaa | tca | cga | tcc | ttg | tat | acc | gtg | cta | cga | tcg | cct | cac | ata | gac | aag | 144 |
| Glu | Ser | Arg | Ser | Leu | Tyr | Thr | Val | Leu | Arg | Ser | Pro | His | Ile | Asp | Lys | |
| | | 35 | | | | | 40 | | | | | 45 | | | | |
| | | | | | | | | | | | | | | | | |
| aag | tcg | agg | gag | cag | ttc | tcg | atg | | | | | | | | | 168 |
| Lys | Ser | Arg | Glu | Gln | Phe | Ser | Met | | | | | | | | | |
| | 50 | | | | | 55 | | | | | | | | | | |

Fig. 1

| | | | | | | | | | | | | | | | | |
|---|---|---|---|---|---|---|---|---|---|---|---|---|---|---|---|---|
| atg | gcc | gcc | gcc | gcc | ctc | ctc | cgc | cgc | tcg | ccg | gcg | gcg | cgc | gcc | ctc | 48 |
| Met | Ala | Ala | Ala | Ala | Leu | Leu | Arg | Arg | Ser | Pro | Ala | Ala | Arg | Ala | Leu | |
| 1 | | | | 5 | | | | | 10 | | | | | 15 | | |

| ctc | tcc | ccg | gcg | ctc | tcc | tcc | cgc | ctc | gtc | gcc | tcc | aag | ccc | cac | tcg | 96 |
| Leu | Ser | Pro | Ala | Leu | Ser | Ser | Arg | Leu | Val | Ala | Ser | Lys | Pro | His | Ser | |
| | | 20 | | | | | | 25 | | | | | 30 | | | |

| tcg | tcc | ccc | gcg | ccg | ccg | ccg | ccg | tcg | aag | gcg | ggg | gcg | aac | acc | | 144 |
| Ser | Ser | Pro | Ala | Pro | Pro | Pro | Pro | Ser | Lys | Ala | Gly | Ala | Asn | Thr | | |
| | | 35 | | | | 40 | | | | | 45 | | | | | |

Fig. 2

| | | | | | | | | | | | | | | | |
|---|---|---|---|---|---|---|---|---|---|---|---|---|---|---|---|
| atg | aga | ggg | tac | aag | ttt | tgc | tgt | gat | ttc | cgg | tac | ctc | ctc | atc | ttg |
| Met | Arg | Gly | Tyr | Lys | Phe | Cys | Cys | Asp | Phe | Arg | Tyr | Leu | Leu | Ile | Leu |
| 1 | | | | 5 | | | | | 10 | | | | | 15 | |

48

| gct | gct | gtc | gcc | ttc | atc | tac | ata | cag | atg | cgg | ctt | ttt | gcg | aca | cag |
|---|---|---|---|---|---|---|---|---|---|---|---|---|---|---|---|
| Ala | Ala | Val | Ala | Phe | Ile | Tyr | Ile | Gln | Met | Arg | Leu | Phe | Ala | Thr | Gln |
| | | | 20 | | | | | 25 | | | | | 30 | | |

96

| tca | gaa | tat | gca | gat | cgc | ctt | gct | gct | gca | att | gaa | gca | gaa | aat | cac |
|---|---|---|---|---|---|---|---|---|---|---|---|---|---|---|---|
| Ser | Glu | Tyr | Ala | Asp | Arg | Leu | Ala | Ala | Ala | Ile | Glu | Ala | Glu | Asn | His |
| | | 35 | | | | | 40 | | | | | 45 | | | |

144

| tgt | aca | agt | cag | acc | aga | ttg | ctt | att | gac | cag | att | agc | cag | cag | caa |
|---|---|---|---|---|---|---|---|---|---|---|---|---|---|---|---|
| Cys | Thr | Ser | Gln | Thr | Arg | Leu | Leu | Ile | Asp | Gln | Ile | Ser | Gln | Gln | Gln |
| | 50 | | | | | 55 | | | | | 60 | | | | |

192

| gga | aga | ata | gtt | gct | ctt | gaa | gaa | caa | atg | aag | cgt | cag | | | |
|---|---|---|---|---|---|---|---|---|---|---|---|---|---|---|---|
| Gly | Arg | Ile | Val | Ala | Leu | Glu | Glu | Gln | Met | Lys | Arg | Gln | | | |
| 65 | | | | | 70 | | | | | 75 | | | | | |

| | | | | | | | | | | | | | | | | |
|---|---|---|---|---|---|---|---|---|---|---|---|---|---|---|---|---|
| atg | gcg | acg | cgc | cgg | gcc | ctc | tcc | tcc | ctc | gtc | cgc | gcc | gcc | tcc | agg | 48 |
| Met | Ala | Thr | Arg | Arg | Ala | Leu | Ser | Ser | Leu | Val | Arg | Ala | Ala | Ser | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctc | cgc | ggg | gcc | tcg | ccc | gcc | ccg | cgc | ccg | cgc | ggg | ccg | ctc | cac | cga | 96 |
| Leu | Arg | Gly | Ala | Ser | Pro | Ala | Pro | Arg | Pro | Arg | Gly | Pro | Leu | His | Arg | |
| | | | 20 | | | | | 25 | | | | | 30 | | | |

| | | | | | | | | | | | | | | | | |
|---|---|---|---|---|---|---|---|---|---|---|---|---|---|---|---|---|
| ccg | tcg | cca | tcg | ggg | tac | ctc | ttc | aac | cgc | gcc | gcc | gcg | tac | gcc | acg | 144 |
| Pro | Ser | Pro | Ser | Gly | Tyr | Leu | Phe | Asn | Arg | Ala | Ala | Ala | Tyr | Ala | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| gcc | gcc | gcg | gcg | aag | gag | cgg | cct | ccc | gcg | ccc | gcg | acg | ggg | aag | gcc | 192 |
| Ala | Ala | Ala | Ala | Lys | Glu | Arg | Pro | Pro | Ala | Pro | Ala | Thr | Gly | Lys | Ala | |
| | 50 | | | | | 55 | | | | | 60 | | | | | |

| | | | | | | | | | | | | | | | | |
|---|---|---|---|---|---|---|---|---|---|---|---|---|---|---|---|---|
| acg | ggt | gga | ggt | aag | atc | acc | gac | gag | ttc | acc | ggc | gcc | ggc | gcc | att | 240 |
| Thr | Gly | Gly | Gly | Lys | Ile | Thr | Asp | Glu | Phe | Thr | Gly | Ala | Gly | Ala | Ile | |
| 65 | | | | | 70 | | | | | 75 | | | | | 80 | |

| | | | | |
|---|---|---|---|---|
| ggg | cag | gtg | tgc | cag | 255 |
| Gly | Gln | Val | Cys | Gln | |
| | | | | 85 | |

Fig. 4

```
atg gca atg gct gtt ttc cgt cgc gaa ggg agg cgt ctc ctc cct tca      48
Met Ala Met Ala Val Phe Arg Arg Glu Gly Arg Arg Leu Leu Pro Ser
1               5                   10                  15 atc gcc gct cgc cca atc gct gct atc cga tct cct ctc tct tct gac      96
Ile Ala Ala Arg Pro Ile Ala Ala Ile Arg Ser Pro Leu Ser Ser Asp
                20                  25                  30 cag gag gaa gga ctt ctt gga gtt cga tct                              126
Gln Glu Glu Gly Leu Leu Gly Val Arg Ser
            35                  40
```

Fig. 5

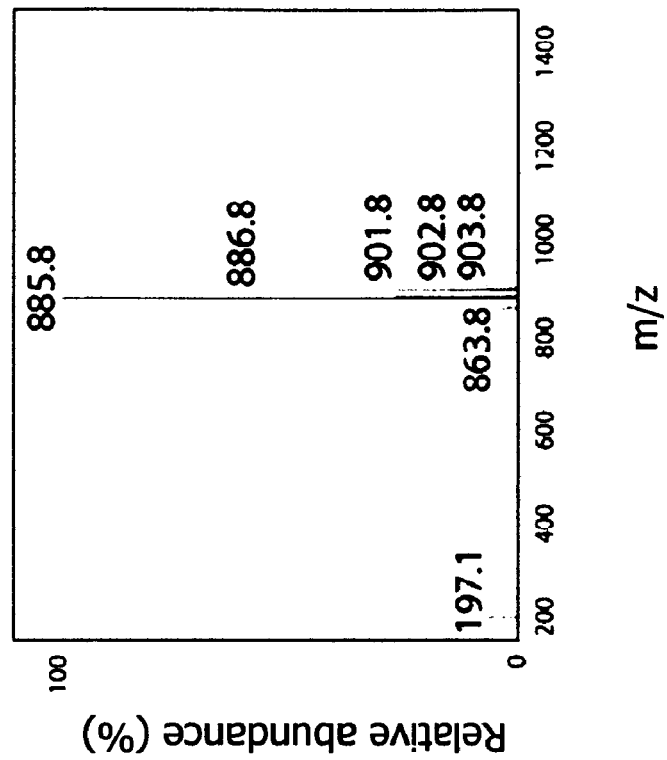
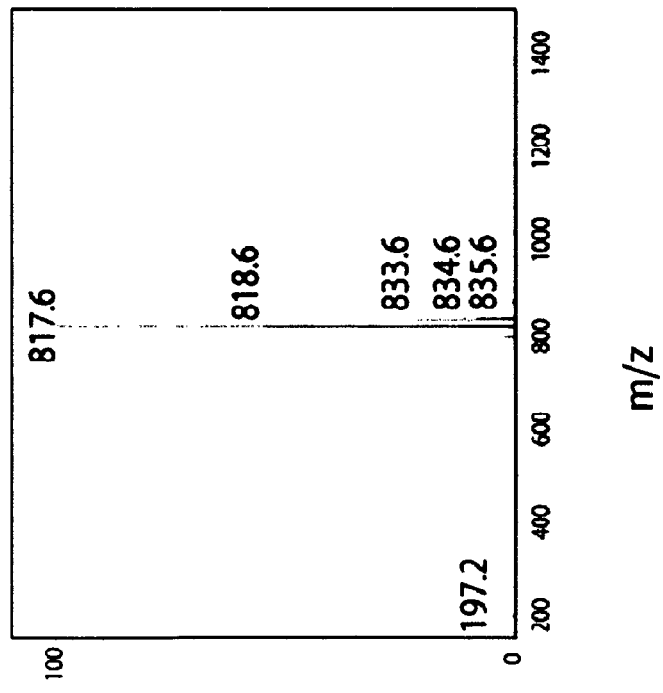
Fig. 9

METHOD FOR PRODUCING UBIQUINONE-10 IN PLANT

This Non-provisional application claims priority under 35 U.S.C. §119(a) to Patent Application No. 2004-136906 filed in Japan on Apr. 30, 2004 and to Patent Application No. 2005-984 filed in Japan on Jan. 5, 2005, the entire contents of which are hereby incorporated by reference.

BACKGROUND OF THE INVENTION

1. Field of the Invention

The present invention relates to a method of producing ubiquinone-10 using a plant, a transgenic plant for use in the production method, and an expression cassette for use in the production of the transgenic plant.

2. Description of the Related Art

Ubiquinone is a component of the electron transfer system and is a compound which has a quinone backbone with an isoprenoid (a naturally-occurring organic compound whose basic unit is isopentenyl diphosphate (IPP) having 5 carbon atoms). Ubiquinone is a biological component which has a structure of 2,3-dimethoxy-5-methyl-6-polyprenyl-1,4-benzoquinone and plays an important role, which is called a coenzyme Q (CoQ). Naturally-occurring ubiquinones include homologs: ubiquinone-5 to ubiquinone-12, depending on the number of side-chain isoprenoid units.

Ubiquinone is present in animal and plant tissue, and microorganisms, in which it plays a physiological and biochemical important role. Ubiquinone is a vitamin-like substance which is also known as an antioxidant substance, and is conformed to have a pharmacological effect for skin aging, immunodeficiency, heart disease, periodontal disease, chronic fatigue syndrome, retrograde brain, neural motor function disorder, diabetes, stroke, arteriosclerosis, cancer, hypertension, hypotension, cerebral infarction, allergic disease and the like. Ubiquinone also has a pharmacological effect to enhance the ability of the heart, and specifically, has a beneficial effect for congestive cardiac failure, and in addition, palpitation/shortness of breath, foot or face swelling, oversensitivity to cold and the like (see Makoto Kawamukai, "Yubikinon no seigosei to atarashii seirikinou [Biosynthesis of ubiquinone and its new physiological function]", Kagaku to Seibutsu [Chemistry and biology], 40 (5); 172-178; Makoto Kawamukai, J. Biosci. Bioeng. 94, 511-517 (2002); and Okada et al., Eur. J. Biochem. 255, 52-59 (1998) for reviews of ubiquinone).

Among the ubiquinones, only ubiquinone-10 (UQ-10) has been confirmed to have a pharmaceutical effect. Ubiquinone-10 is synthesized in the body, however, its amount is decreased due to aging, fatigue, stress or the like, and therefore, needs to be often supplied. Therefore, at present time, ubiquinone-10 is contained in not only medicaments but also cosmetics and sports drinks, and is also sold as an ingredient of health food and dietary supplement.

Ubiquinone-10 is currently extracted and purified from plants in the family Solanaceae, yeast or microorganisms. However, the production does not keep up with demand. There is a need for a production method in addition to the conventional techniques.

Isoprenoid which forms a side-chain of ubiquinone is a naturally-occurring organic compound whose basic unit is isopentenyl diphosphate (IPP) having 5 carbon atoms. A large amount of isoprenoid is present in nature. In addition to that, isoprenoid is used as a side-chain of ubiquinone, isoprenoid is known as a part of carotenoids, natural rubbers, or prenylated proteins. Isoprenoid is gradually synthesized into a long chain by binding a new IPP to a basic IPP or FPP (farnesyl diphosphate) during biosynthesis in organisms.

It is known that a decaprenyl diphosphate synthase gene (SEQ ID NO. 5), which is cloned from a bacterium *Gluconobacter suboxydans*, produces ubiquinone-10 when expressed in *E. coli* (Japanese Laid-Open Publication No. 10-57072; and Okada et al., Eur. J. Biochem. 255, 52-59 (1998)). However, when ubiquinone-10 is produced in a bacterium, such as *E. coli*, production of dietary supplements, foods, beverages, food additives and the like which contain ubiquinone-10, requires enormous cost and effort to purify ubiquinone-10. In contrast, when ubiquinone-10 is expressed in an edible plant, the cost and effort for the purification can be reduced. However, there has been no report that the above-described bacterial gene is expressed in plants to produce ubiquinone-10.

On the other hand, an attempt has been made to use a eukaryote (recombinant fission yeast) to produce ubiquinone-10 (Japanese Laid-Open Publication No. 9-173076). In Japanese Laid-Open Publication No. 9-173076, the decaprenyl synthase gene of the fission yeast *S. pombe* was cloned and sequenced, and a fusion gene linked with a mitchondrial targeting signal was used to transform the budding yeast *S. cerevisiae*. However, production of ubiquinone-10 in the recombinant yeast cell has not been confirmed. Moreover, it is suggested that enzyme activity is low in the recombinant yeast cell. In contrast, yeast expressing ddsA gene from *Gluconobacter* produced ubiquinone-10. Therefore, no technique of producing ubiquinone-10 using a recombinant cell except for *E. coli* and yeast has been established to date.

Therefore, there is a demand for a method of enhancing production of ubiquinone-10 using a transformed plant, and a plant having an enhanced amount of ubiquinone-10 production.

An object of the present invention is to provide a method of producing ubiquinone-10 in a transgenic plant, and a transgenic plant for producing ubiquinone-10. Another object of the present invention is to provide an expression cassette for use in preparation of the transgenic plant of the present invention. Still another object of the present invention is to provide a composition, a food additive, a supplement and a pharmaceutical composition which contain ubiquinone-10 produced by the plant.

SUMMARY OF THE INVENTION

The present invention provides a plant which produces ubiquinone-10. The plant is produced by targeting of a decaprenyl diphosphate synthase gene to the mitochondria and/or the Golgi apparatuses in plants.

The present invention provides the following.

1. A plant which is transformed using an expression cassette which expresses polyprenyl diphosphate synthase.

2. A plant according to item 1, wherein the polyprenyl diphosphate synthase is decaprenyl diphosphate synthase.

3. A plant according to item 1, wherein the decaprenyl diphosphate synthase is an enzyme derived from a bacterium.

4. A plant according to item 3, wherein the decaprenyl diphosphate synthase is an enzyme derived from *Gluconobacter suboxydans*.

5. A plant according to item 2, wherein the decaprenyl diphosphate synthase is encoded by a nucleic acid hybridizable to a nucleic acid having a sequence set forth in SEQ ID NO. 5 under stringent conditions.

6. A plant according to item 2, wherein the decaprenyl diphosphate synthase is encoded by a nucleic acid obtained by introducing one or several deletions, additions or substitutions into a nucleic acid sequence of SEQ ID NO. 5.

7. A plant according to item 2, wherein the decaprenyl diphosphate synthase is encoded by a nucleic acid having a sequence which has more than 80% identity with a nucleic acid sequence set forth in SEQ ID NO. 5.

8. A plant according to item 2, wherein the decaprenyl diphosphate synthase has an amino acid sequence obtained by introducing one or several deletions, additions or substitutions into an amino acid sequence set forth in SEQ ID NO. 6.

9. A plant according to item 2, wherein the decaprenyl diphosphate synthase has an amino acid sequence which has more than 80% identity with an amino acid sequence of SEQ ID NO. 6.

10. A plant according to item 2, wherein a nucleic acid encoding the decaprenyl diphosphate synthase is operatively linked with a nucleic acid encoding a mitochondrial targeting sequence.

11. A plant according to item 10, wherein the nucleic acid encoding the mitochondrial targeting sequence is selected from the group consisting of a nucleic acid encoding a fragment of rice RPS10 protein (SEQ ID NO. 2), a nucleic acid encoding a fragment of RPS14 protein (SEQ ID NO. 4), a nucleic acid encoding a fragment of RPS11 protein, a nucleic acid encoding a fragment of ATPase β-subunit protein (SEQ ID NO. 10), and a nucleic acid encoding a fragment of ATPase γ-subunit protein (SEQ ID NO. 12).

12. A plant according to item 10, wherein the mitochondrial targeting sequence is a fragment consisting of amino acids 1 to 56 of rice RPS10 protein (SEQ ID NO. 2).

13. A plant according to item 10, wherein the mitochondrial targeting sequence is encoded by a nucleic acid hybridizable to a nucleic acid encoding an amino acid sequence of amino acids 1 to 56 of rice RPS10 protein (SEQ ID NO. 2) under stringent conditions.

14. A plant according to item 10, wherein the mitochondrial targeting sequence is encoded by a nucleic acid obtained by introducing one or several deletions, additions or substitutions into a nucleic acid sequence encoding an amino acid sequence of amino acids 1 to 56 of rice RPS10 protein (SEQ ID NO. 2), or a fragment of the nucleic acid sequence encoding the amino acid sequence of amino acids 1 to 56 of the rice RPS10 protein (SEQ ID NO. 2).

15. A plant according to item 10, wherein the mitochondrial targeting sequence is encoded by a nucleic acid having a sequence which has more than 80% identity with a nucleic acid sequence encoding an amino acid sequence of amino acids 1 to 56 of rice RPS10 protein (SEQ ID NO. 2).

16. A plant according to item 10, wherein the mitochondrial targeting sequence has an amino acid sequence obtained by introducing one or several deletions, additions or substitutions into an amino acid sequence of amino acids 1 to 56 of rice RPS10 protein (SEQ ID NO. 2), or a fragment of the amino acid sequence of amino acids 1 to 56 of the rice RPS10 protein (SEQ ID NO. 2).

17. A plant according to item 10, wherein the mitochondrial targeting sequence has an amino acid sequence which has more than 80% identity with an amino acid sequence of amino acids 1 to 56 of rice RPS10 protein (SEQ ID NO. 2).

18. A plant according to item 10, wherein the mitochondrial targeting sequence is a fragment consisting of an amino acid sequence of amino acids 1 to 48 of rice RPS14 protein (SEQ ID NO. 4).

19. A plant according to item 10, wherein the mitochondrial targeting sequence is encoded by a nucleic acid hybridizable to a nucleic acid encoding an amino acid sequence of amino acids 1 to 48 of rice RPS14 protein (SEQ ID NO. 4) under stringent conditions.

20. A plant according to item 10, wherein the mitochondrial targeting sequence is encoded by a nucleic acid obtained by introducing one or several deletions, additions or substitutions into a nucleic acid sequence encoding an amino acid sequence of amino acids 1 to 48 of rice RPS14 protein (SEQ ID NO. 4), or a fragment of a nucleic acid sequence encoding the amino acid sequence of amino acids 1 to 48 of the rice RPS14 protein (SEQ ID NO. 4).

21. A plant according to item 10, wherein the mitochondrial targeting sequence is encoded by a nucleic acid having a sequence which has more than 80% identity with a nucleic acid sequence encoding an amino acid sequence of amino acids 1 to 48 of rice RPS14 protein (SEQ ID NO. 4).

22. A plant according to item 10, wherein the mitochondrial targeting sequence has an amino acid sequence obtained by introducing one or several deletions, additions or substitutions into an amino acid sequence of amino acids 1 to 48 of rice RPS14 protein (SEQ ID NO. 4), or a fragment of the amino acid sequence of amino acids 1 to 48 of the rice RPS14 protein (SEQ ID NO. 4).

23. A plant according to item 10, wherein the mitochondrial targeting sequence has an amino acid sequence which has more than 80% identity with an amino acid sequence of amino acids 1 to 48 of rice RPS14 protein (SEQ ID NO. 4).

24. A plant according to item 2, wherein the polyprenyl diphosphate synthase is operatively linked with a Golgi apparatus targeting sequence.

25. A plant according to item 24, wherein a nucleic acid encoding the Golgi apparatus targeting sequence is a nucleic acid encoding a fragment of tobacco N-acetylglucosaminyl transferase I protein (SEQ ID NO. 8).

26. A plant according to item 24, wherein the Golgi apparatus targeting sequence is a fragment consisting of an amino acid sequence of amino acids 1 to 77 of the tobacco N-acetylglucosaminyl transferase I protein (SEQ ID NO. 8).

27. A plant according to item 24, wherein the Golgi apparatus targeting sequence is encoded by a nucleic acid hybridizable to a nucleic acid encoding an amino acid sequence of amino acids 1 to 77 of tobacco N-acetylglucosaminyl transferase I protein (SEQ ID NO. 8) under stringent conditions.

28. A plant according to item 24, wherein the Golgi apparatus targeting sequence is encoded by a nucleic acid obtained by introducing one or several deletions, additions or substitutions into a nucleic acid sequence encoding an amino acid sequence of amino acids 1 to 77 of tobacco N-acetylglucosaminyl transferase I protein (SEQ ID NO. 8), or a fragment of the nucleic acid sequence encoding the amino acid sequence of amino acids 1 to 77 of the tobacco N-acetylglucosaminyl transferase I protein (SEQ ID NO. 8).

29. A plant according to item 24, wherein the Golgi apparatus targeting sequence is encoded by a nucleic acid having a sequence which has 80% identity with a nucleic acid sequence encoding an amino acid sequence of amino acids 1 to 77 of tobacco N-acetylglucosaminyl transferase I protein (SEQ ID NO. 8).

30. A plant according to item 24, wherein the Golgi apparatus targeting sequence has an amino acid sequence obtained by introducing one or several deletions, additions or substitutions into an amino acid sequence of amino acids 1 to 77 of tobacco N-acetylglucosaminyl transferase I protein (SEQ ID NO. 8), or a fragment of the amino acid sequence of amino acids 1 to 77 of the tobacco N-acetylglucosaminyl transferase I protein (SEQ ID NO. 8).

31. A plant according to item 24, wherein the Golgi apparatus targeting sequence has an amino acid sequence which has 80% identity with an amino acid sequence of amino acids 1 to 77 of tobacco N-acetylglucosaminyl transferase I protein (SEQ ID NO. 8).

32. A plant according to item 1, wherein the polyprenyl diphosphate synthase gene is operatively linked with a seed-specific promoter.

33. A plant according to item 1, where in the plant is selected from the group consisting of a plant cell, a plant culture cell, a plant seed, a regenerated plant, a plant callus, plant tissue, a leaf, a stem, a root, a flower, a seeding, an alga, a fern, and a moss.

34. A plant according to item 1, wherein the plant is a monocotyledon.

35. A plant according to item 1, wherein the plant is a dicotyledon.

36. A seed from a plant according to any one of items 1, 32, 34, or 35.

37. A plant according to item 35, wherein the monocotyledon is selected from the group consisting of rice, maize, oat, wheat, barley, buckwheat, Job's-tears, wild oat, billion-dollar grass, banana, and sugarcane.

38. A plant according to item 36, wherein the dicotyledon is selected from the group consisting of soybean, tomato, potato, sweet potato, almond, pistachio, peanut, hazel, walnut, cashew, and sesame.

39. An expression cassette for causing polyprenyl diphosphate synthase to be expressed in a plant.

40. An expression cassette according to item 39, wherein the polyprenyl diphosphate synthase is decaprenyl diphosphate synthase.

41. An expression cassette according to item 39, wherein the decaprenyl diphosphate synthase is an enzyme derived from a bacterium.

42. An expression cassette according to item 41, wherein the decaprenyl diphosphate synthase is an enzyme derived from *Gluconobacter suboxydans*.

43. An expression cassette according to item 40, wherein the decaprenyl diphosphate synthase is encoded by a nucleic acid hybridizable to a nucleic acid set forth in SEQ ID NO. 5 under stringent conditions.

44. An expression cassette according to item 40, wherein the decaprenyl diphosphate synthase is encoded by a nucleic acid obtained by introducing one or several deletions, additions or substitutions into a nucleic acid sequence set forth in SEQ ID NO. 5, or a fragment of nucleic acid having sequence set forth in SEQ ID NO. 5.

45. An expression cassette according to item 40, wherein the decaprenyl diphosphate synthase is encoded by a nucleic acid having a sequence which has more than 80% identity with a nucleic acid sequence set forth in SEQ ID NO. 5.

46. An expression cassette according to item 40, wherein the decaprenyl diphosphate synthase has an amino acid sequence obtained by introducing one or several deletions, additions or substitutions into an amino acid sequence set forth in SEQ ID NO. 6, or fragment of the amino acid sequence set forth in SEQ ID NO. 6.

47. An expression cassette according to item 40, wherein the decaprenyl diphosphate synthase has an amino acid sequence which has more than 80% identity with an amino acid sequence set forth in SEQ ID NO. 6.

48. An expression cassette according to item 40, wherein a nucleic acid encoding the decaprenyl diphosphate synthase is operatively linked with a nucleic acid encoding a mitochondrial targeting sequence.

49. An expression cassette according to item 48, wherein the nucleic acid encoding the mitochondrial targeting sequence is selected from the group consisting of a nucleic acid encoding a fragment of rice RPS10 protein (SEQ ID NO. 2), a nucleic acid encoding a fragment of RPS14 protein (SEQ ID NO. 4), a nucleic acid encoding a fragment of RPS11 protein, a nucleic acid encoding a fragment of ATPase β-subunit protein (SEQ ID NO. 10), and a nucleic acid encoding a fragment of ATPase γ-subunit protein (SEQ ID NO. 12).

50. An expression cassette according to item 48, wherein the mitochondrial targeting sequence is a fragment consisting of amino acids 1 to 56 of rice RPS10 protein (SEQ ID NO. 2).

51. An expression cassette according to item 48, wherein the mitochondrial targeting sequence is encoded by a nucleic acid hybridizable to a nucleic acid encoding an amino acid sequence of amino acids 1 to 56 of rice RPS10 protein (SEQ ID NO. 2) under stringent conditions.

52. An expression cassette according to item 48, wherein the mitochondrial targeting sequence is encoded by a nucleic acid obtained by introducing one or several deletions, additions or substitutions into a nucleic acid sequence encoding an amino acid sequence of amino acids 1 to 56 of rice RPS10 protein (SEQ ID NO. 2), or a fragment of the nucleic acid sequence encoding the amino acid sequence of amino acids 1 to 56 of the rice RPS10 protein (SEQ ID NO. 2).

53. An expression cassette according to item 48, wherein the mitochondrial targeting sequence is encoded by a nucleic acid having a sequence which has more than 80% identity with a nucleic acid sequence encoding an amino acid sequence of amino acids 1 to 56 of rice RPS10 protein (SEQ ID NO. 2).

54. An expression cassette according to item 48, wherein the mitochondrial targeting sequence has an amino acid sequence obtained by introducing one or several deletions, additions or substitutions into an amino acid sequence of amino acids 1 to 56 of rice RPS10 protein (SEQ ID NO. 2), or a fragment of the amino acid sequence of amino acids 1 to 56 of the rice RPS10 protein (SEQ ID NO. 2).

55. An expression cassette according to item 48, wherein the mitochondrial targeting sequence has an amino acid sequence which has more than 80% identity with an amino acid sequence of amino acids 1 to 56 of rice RPS10 protein (SEQ ID NO. 2).

56. An expression cassette according to item 48, wherein the mitochondrial targeting sequence is a fragment consisting of an amino acid sequence of amino acids 1 to 48 of rice RPS14 protein (SEQ ID NO. 4).

57. An expression cassette according to item 48, wherein the mitochondrial targeting sequence is encoded by a nucleic acid hybridizable to a nucleic acid encoding an amino acid sequence of amino acids 1 to 48 of rice RPS14 protein (SEQ ID NO. 4) under stringent conditions.

58. An expression cassette according to item 48, wherein the mitochondrial targeting sequence is encoded by a nucleic acid obtained by introducing one or several deletions, additions or substitutions into a nucleic acid sequence encoding an amino acid sequence of amino acids 1 to 48 of rice RPS14 protein (SEQ ID NO. 4), or a fragment of a nucleic acid sequence encoding the amino acid sequence of amino acids 1 to 48 of the rice RPS14 protein (SEQ ID NO. 4).

59. An expression cassette according to item 48, wherein the mitochondrial targeting sequence is encoded by a nucleic acid having a sequence which has more than 80% identity with a nucleic acid sequence encoding an amino acid sequence of amino acids 1 to 48 of rice RPS14 protein (SEQ ID NO. 4).

60. An expression cassette according to item 48, wherein the mitochondrial targeting sequence has an amino acid sequence obtained by introducing one or several deletions, additions or substitutions into an amino acid sequence of amino acids 1 to 48 of rice RPS14 protein (SEQ ID NO. 4), or a fragment of the amino acid sequence of amino acids 1 to 48 of the rice RPS14 protein (SEQ ID NO. 4).

61. An expression cassette according to item 48, wherein the mitochondrial targeting sequence has an amino acid sequence which has more than 80% identity with an amino acid sequence of amino acids 1 to 48 of rice RPS14 protein (SEQ ID NO. 4).

62. An expression cassette according to item 39, wherein the polyprenyl diphosphate synthase is operatively linked with a Golgi apparatus targeting sequence.

63. An expression cassette according to item 62, wherein a nucleic acid encoding the Golgi apparatus targeting sequence is a nucleic acid encoding a fragment of tobacco N-acetylglucosaminyl transferase I protein (SEQ ID NO. 8).

64. An expression cassette according to item 62, wherein the Golgi apparatus targeting sequence is a fragment consisting of an amino acid sequence of amino acids 1 to 77 of the tobacco N-acetylglucosaminyl transferase I protein (SEQ ID NO. 8).

65. An expression cassette according to item 62, wherein the Golgi apparatus targeting sequence is encoded by a nucleic acid hybridizable to a nucleic acid encoding an amino acid sequence of amino acids 1 to 77 of tobacco N-acetylglucosaminyl transferase I protein (SEQ ID NO. 8) under stringent conditions.

66. An expression cassette according to item 62, wherein the Golgi apparatus targeting sequence is encoded by a nucleic acid obtained by introducing one or several deletions, additions or substitutions into a nucleic acid sequence encoding an amino acid sequence of amino acids 1 to 77 of tobacco N-acetylglucosaminyl transferase I protein (SEQ ID NO. 8), or a fragment of the nucleic acid sequence encoding the amino acid sequence of amino acids 1 to 77 of the tobacco N-acetylglucosaminyl transferase I protein (SEQ ID NO. 8).

67. An expression cassette according to item 62, wherein the Golgi apparatus targeting sequence is encoded by a nucleic acid having a sequence which has 80% identity with a nucleic acid sequence encoding an amino acid sequence of amino acids 1 to 77 of tobacco N-acetylglucosaminyl transferase I protein (SEQ ID NO. 8).

68. An expression cassette according to item 62, wherein the Golgi apparatus targeting sequence has an amino acid sequence obtained by introducing one or several deletions, additions or substitutions into an amino acid sequence of amino acids 1 to 77 of tobacco N-acetylglucosaminyl transferase I protein (SEQ ID NO. 8), or a fragment of the amino acid sequence of amino acids 1 to 77 of the tobacco N-acetylglucosaminyl transferase I protein (SEQ ID NO. 8).

69. An expression cassette according to item 62, wherein the Golgi apparatus targeting sequence has an amino acid sequence which has 80% identity with an amino acid sequence of amino acids 1 to 77 of tobacco N-acetylglucosaminyl transferase I protein (SEQ ID NO. 8).

70. An expression cassette according to item 39, wherein the polyprenyl diphosphate synthase gene is operatively linked with a seed-specific promoter.

71. A plant which contains an expression cassette according to item 70.

72. A seed of a plant according to item 71.

73. A method for producing ubiquinone-10 using a plant, comprising:
    preparing a plant according to item 1; and
    culturing the plant.

74. A method for producing ubiquinone-10 using a plant, comprising:
    introducing an expression cassette according to item 37 into the plant; and
    culturing the plant into which the expression cassette is introduced.

75. Plant tissue which is obtained from a plant according to item 1 and contains ubiquinone-10.

76. A plant cell which is obtained from a plant according to item 1 and contains ubiquinone-10.

77. A food which contains ubiquinone-10 derived from a plant according to item 1.

78. A food according to item 77, further containing an ingredient derived from the plant according to item 1.

79. A food according to item 78, wherein the ingredient derived from the plant according to item 1 is a protein.

80. A composition which contains ubiquinone-10 derived from a plant according to item 1.

81. A composition according to item 80, further containing an ingredient derived from the plant according to item 1.

82. A composition according to item 81, wherein the ingredient derived from the plant according to item 1 is a protein.

83. A food additive which contains ubiquinone-10 derived from a plant according to item 1.

84. A food additive according to item 83, further containing an ingredient derived from the plant according to item 1.

85. A food additive according to item 84, wherein the ingredient derived from the plant according to item 1 is a protein.

86. A cosmetic which contains ubiquinone-10 derived from a plant according to item 1.

87. A cosmetic according to item 86, further containing an ingredient derived from the plant according to item 1.

88. A cosmetic according to item 87, wherein the ingredient derived from the plant according to item 1 is a protein.

89. A beverage which contains ubiquinone-10 derived from a plant according to item 1.

90. A beverage according to item 89, further containing an ingredient derived from the plant according to item 1.

91. A beverage according to item 90, wherein the ingredient derived from the plant according to item 1 is a protein.

92. A leaf which contains ubiquinone-10 derived from a plant according to item 1.

93. An embryo which contains ubiquinone-10 derived from a plant according to item 1.

94. A fruit which contains ubiquinone-10 derived from a plant according to item 1.

95. A stem which contains ubiquinone-10 derived from a plant according to item 1.

96. A root which contains ubiquinone-10 derived from a plant according to item 1.

97. A flower which contains ubiquinone-10 derived from a plant according to item 1.

98. A seed which contains ubiquinone-10 derived from a plant according to item 1.

99. A rice bran which contains ubiquinone-10 derived from a plant according to item 1.

100. A rice cell or tissue which contains ubiquinone-10.

101. A rice cell or tissue according to item 100, which is a seed.

102. A rice cell or tissue according to item 100, which is a brown rice.

Thus, the invention described herein makes possible the advantages of providing a method for producing ubiquinone-10 using a plant, a transgenic plant for use in the method, and an expression cassette for use in production of the transgenic plant, and further, a composition, a food additive, a supplement and a pharmaceutical composition which contain ubiquinone-10 produced by the plant.

These and other advantages of the present invention will become apparent to those skilled in the art upon reading and understanding the following detailed description with reference to the accompanying figures.

BRIEF DESCRIPTION OF THE DRAWINGS

FIG. 1 shows a nucleic acid sequence and an amino acid sequence of a mitochondrial targeting sequence of rice RPS10.

FIG. 2 shows a nucleic acid sequence and an amino acid sequence of a mitochondrial targeting sequence of rice RPS14.

FIG. 3 shows a nucleic acid sequence and an amino acid sequence of a Golgi apparatus targeting sequence of tobacco N-acetylglucosaminyl transferase I.

FIG. 4 shows a nucleic acid sequence and an amino acid sequence of a mitochondrial targeting sequence of rice ATPase β-subunit protein.

FIG. 5 shows a nucleic acid sequence and an amino acid sequence of a mitochondrial targeting sequence of *Arabidopsis* ATPase γ-subunit protein.

FIG. 9 shows the molecular mass of ubiquinone-9 produced in the wild type plant (A) and ubiquinone-10 produced in S14:ddsA plants (B).

DESCRIPTION OF THE SEQUENCES

Figure 6:
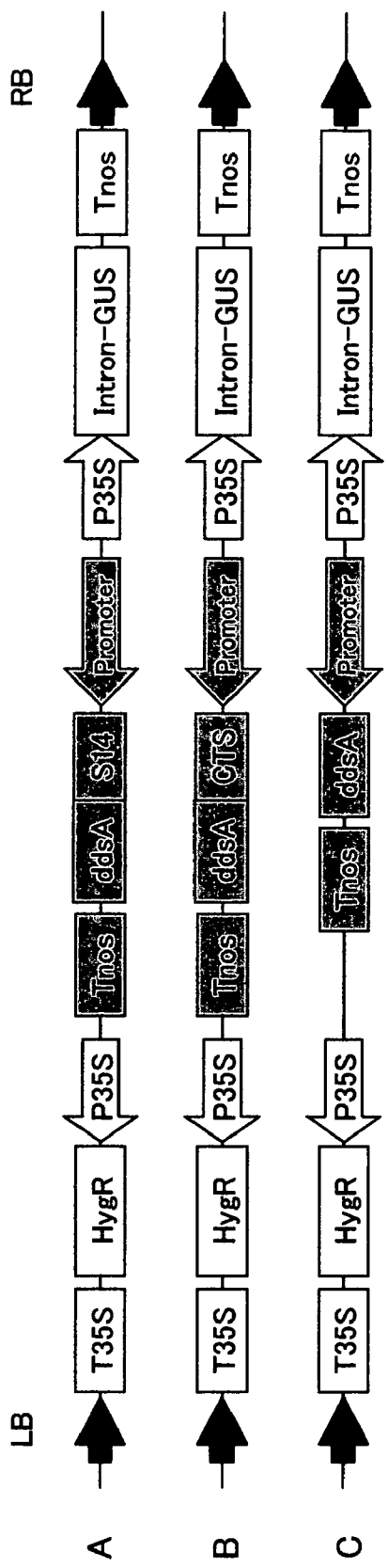
FIG. 6 shows an expression cassette for use in production of a transgenic plant of the present invention. T35S represents a terminator for a CaMV35S gene; HygR represents a hygromycin-resistant gene; P35S represents a CaMV35S promoter; Tnos represents a terminator for nopaline synthase; ddsA represents a *Gluconobacter suboxydans*-derived decaprenyl diphosphate synthase gene; S14 represents a mitochondrial targeting sequence (amino acids 1 to 48) of RPS14 protein; CTS represents a Golgi apparatus targeting signal (amino acids 1 to 77) located at an N terminus of tobacco N-acetylglucosaminyl transferase I (GnT1); Promoter represents a CaMV35S promoter; Intron-GUS represents a GUS gene including an intron; LB represents a left border sequence; and RB represents a right border sequence.

SEQ ID NO. 1: a nucleic acid sequence (genomic sequence) of rice RPS10 gene.

SEQ ID NO. 2: an amino acid sequence of rice RPS10. An amino acid sequence of amino acids 1 to 56 can be used as a mitochondrial targeting sequence.

SEQ ID NO. 3: a nucleic acid sequence (cDNA sequence) of rice RPS14 gene.

SEQ ID NO. 4: an amino acid sequence of rice RPS14. An amino acid sequence of amino acids 1 to 48 can be used as a mitochondrial targeting sequence.

SEQ ID NO. 5: a nucleic acid sequence (cDNA sequence) of a *Gluconobacter suboxydans* ddsA gene.

SEQ ID NO. 6: an amino acid sequence of *Gluconobacter suboxydans*-derived decaprenyl diphosphate synthase.

SEQ ID NO. 7: a nucleic acid sequence (cDNA sequence) encoding tobacco N-acetylglucosaminyl transferase I protein.

SEQ ID NO. 8: an amino acid sequence of tobacco N-acetylglucosaminyl transferase I protein. An amino acid sequence of amino acids 1 to 77 can be used as a Golgi apparatus targeting sequence.

SEQ ID NO. 9: a nucleic acid sequence (cDNA sequence) encoding rice ATPase β-subunit protein.

SEQ ID NO. 10: an amino acid sequence of rice ATPase β-subunit protein. An amino acid sequence of amino acids 1 to 85 can be used as a mitochondrial targeting sequence.

SEQ ID NO. 11: a nucleic acid sequence (cDNA sequence) encoding *Arabidopsis* ATPase γ-subunit protein.

SEQ ID NO. 12: an amino acid sequence of *Arabidopsis* ATPase γ-subunit protein. An amino acid sequence of amino acids 1 to 42 can be used as a mitochondrial targeting sequence.

DESCRIPTION OF THE PREFERRED EMBODIMENTS

Hereinafter, the present invention will be described. It should be understood throughout the present specification that articles for singular forms include the concept of their plurality unless otherwise mentioned. It should also be understood that terms as used herein have definitions ordinarily used in the art unless otherwise mentioned.

Hereinafter, terms particularly used herein will be defined.

As used herein, the term "plant" is a generic term encompassing organisms belonging to the plant kingdom, characteristically containing chlorophyll, having rigid cell walls, permanently producing abundant embryonic tissue, and lacking the power of locomotion. Typically, a plant refers to a flowering plant which forms cell walls and has anabolism by chlorophyll. "Plant" includes any of monocotyledonous and dicotyledonous plants, and an alga, fern, and a moss. Examples of monocotyledons include Gramineae plants. Examples of preferable monocotyledons include, but are not limited to, maize, sugarcane, wheat, rice, oat, barley, Sorghum, rye, billion-dollar grass, banana, and foxtail millet, and more preferably maize, wheat, rice and sugarcane. Examples of dicotyledons include, but are not limited to, brassicaceous plants, leguminous plants, solanaceous plants, cucurbitaceous plants, and convolvulaceous plants. Examples of dicotyledons include, but are not limited to, soybean, tomato, potato, sweet potato, almond, pistachio, peanut, hazel, walnut, cashew, and sesame. A plant means any of a whole plant, a plant organ, plant tissue, a plant cell, and a seed unless otherwise specified. Examples of a plant organ include a fruit, a seed, a root, a leaf, a stem, a flower, an embryo, and the like. Examples of a plant cell include a callus and a suspension culture cell. Rice bran and embryo may be used as a source of recombinantly produced ubiquinone-10. In a particular embodiment, a plant may mean an individual plant.

Examples of plants of the family Gramineae include plants of the genera *Oryza, Triticum, Hordeum, Secale, Saccharum, Sorghum*, and *Zea* (e.g., rice, wheat, barley, rye, sugarcane, sorghum, maize, etc.).

As used herein, the term "modified plant" refers to a plant in which at least a portion of the structure and/or function of genomic information thereof is changed as compared to a naturally-occurring plant. Such a modified plant may be produced, for example, by transformation of a wild type plant, crossbreeding with a transformed plant, suppression of gene expression with an antisense nucleic acid, suppression of gene expression by RNA interference, or the like. A method for producing a modified plant is not limited as such.

The terms "polynucleotide", "oligonucleotide", and "nucleic acid" as used herein have the same meaning and refer to a nucleotide polymer having any length. This term also includes an "oligonucleotide derivative" or a "polynucleotide derivative". The terms "derivative oligonucleotide" and "derivative polynucleotide" are interchangeably used to refer to oligonucleotides or polynucleotides containing a derivative of a nucleotide or having a different link between nucleotides from a normal link. Examples of such an oligonucleotide specifically include 2'-O-methyl-ribonucleotide, an oligonucleotide derivative in which a phosphodiester bond in an oligonucleotide is converted to a phosphorothioate bond, an oligonucleotide derivative in which a phosphodiester bond in an oligonucleotide is converted to a N3'-P5' phosphoroamidate bond, an oligonucleotide derivative in which a ribose and a phosphodiester bond in an oligonucleotide are converted to a peptide-nucleic acid bond, an oligonucleotide derivative in which uracil in an oligonucleotide is substituted with C-5 propynyl uracil, an oligonucleotide derivative in which uracil in an oligonucleotide is substituted with C-5 thiazole uracil, an oligonucleotide derivative in which cytosine in an oligonucleotide is substituted with C-5 propynyl cytosine, an oligonucleotide derivative in which cytosine in an oligonucleotide is substituted with phenoxazine-modified cytosine, an oligonucleotide derivative in which ribose in DNA is substituted with 2'-O-propyl ribose, and an oligonucleotide derivative in which ribose in an oligonucleotide is substituted with 2'-methoxyethoxy ribose. Unless otherwise indicated, a particular nucleic acid sequence also implicitly encompasses conservatively-modified variants thereof (e.g. degenerate codon substitutions) and complementary sequences as well as the sequence explicitly indicated. Specifically, degenerate codon substitutions may be produced by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term "nucleic acid" is herein used interchangeably with "gene", "cDNA", "mRNA", "oligonucleotide", and "polynucleotide". A particular nucleic acid sequence also implicitly encompasses "splice variants". Similarly, a particular protein encoded by a nucleic acid implicitly encompasses any protein encoded by a splice variant of that nucleic acid. "Splice variants", as the name suggests, are products of alternative splicing of a gene. After transcription, an initial nucleic acid transcript may be spliced such that different (alternative) nucleic acid splice products encode different polypeptides. Mechanisms for the production of splice variants vary, but include alternative splicing of exons. Alternative polypeptides derived from the same nucleic acid by readthrough transcription are also encompassed by this definition. Any products of a splicing reaction, including recombinant forms of the splice products, are included in this definition.

As used herein, the term "gene" refers to an element defining a genetic trait. A gene is typically arranged in a given sequence on a chromosome. A gene which defines the primary structure of a protein is called a structural gene. A gene which regulates the expression of a structural gene is called a regulatory gene. As used herein, "gene" may refer to "polynucleotide", "oligonucleotide", "nucleic acid", and "nucleic acid molecule" and/or "protein", "polypeptide", "oligopeptide" and "peptide". As used herein, "homology" of a gene refers to the magnitude of identity between two or more gene sequences. Therefore, the greater the homology between two genes, the greater the identity or similarity between their sequences. Whether or not two genes have homology can be determined by comparing their sequences directly or by a hybridization method under stringent conditions. When two gene sequences are directly compared with each other, the genes have homology if the DNA sequences of the genes have typically at least 50%, preferably at least 70%, more preferably at least 80%, 90%, 95%, 96%, 97%, 98%, or 99% identity to each other.

As used herein, the term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, Molecular Cloning: A Laboratory Manual (2nd ed., Cold Spring Harbor Laboratory, 1989); Anderson et al., Nucleic Acid Hybridization: A Practical Approach Ch. 4 (IRL Press Limited).

More stringent conditions (such as higher temperature, lower ionic strength, higher formamide, or other denaturing agents) may be used, however, the rate of hybridization will be affected. Other agents may be included in the hybridization and washing buffers for the purpose of reducing non-specific and/or background hybridization. Examples are 0.1% bovine serum albumin, 0.1% polyvinylpyrrolidone, 0.1% sodium pyrophosphate, 0.1% sodium dodecylsulfate NaDodSO$_4$ (SDS), Ficoll, Denhardt's solution, sonicated salmon sperm DNA (or another noncomplementary DNA), and dextran sulfate, although other suitable agents can also be used. The concentration and types of these additives can be changed without substantially affecting the stringency of the hybridization conditions. Hybridization experiments are ordinarily carried out at pH 6.8-7.4; however, at typical ionic strength conditions, the rate of hybridization is nearly independent of pH. See Anderson et al., Nucleic Acid Hybridization: A Practical Approach Ch. 4 (IRL Press Limited).

Factors affecting the stability of DNA duplex include base composition, length, and degree of base pair mismatch. Hybridization conditions can be adjusted by those skilled in the art in order to accommodate these variables and allow DNAs of different sequence relatedness to form hybrids. The melting temperature of a perfectly matched DNA duplex can be estimated by the following equation:

$$Tm \,(^\circ C.)=81.5+16.6\,(\log\,[Na^+])+0.41\,(\%\,G+C)-600/N-0.72\,(\%\,\text{formamide})$$

where N is the length of the duplex formed, [Na$^+$] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, hybridization in "moderately stringent conditions" of 50° C. in 0.015 M sodium ion will allow about a 21% mismatch.

It will be appreciated by those skilled in the art that there is no absolute distinction between "highly stringent conditions" and "moderately stringent conditions". For example, at 0.015 M sodium ion (no formamide), the melting temperature of perfectly matched DNA is about 71° C. A wash at 65° C. (at the same ionic strength) would allow for approximately a 6% mismatch. To capture more distantly related sequences, those skilled in the art can simply lower the temperature or raise the ionic strength.

A good estimate of the melting temperature in 1 M NaCl for oligonucleotide probes up to about 20 nucleotides is given by:

$$Tm=(2^\circ C.\text{ per }A-T\text{ base pair})+(4^\circ C.\text{ per }G-C\text{ base pair}).$$

Note that the sodium ion concentration in 6× Standard Saline Citrate (SSC) is 1 M. See Suggs et al., Developmental Biology Using Purified Genes 683 (Brown and Fox, eds., 1981).

High stringency washing conditions for oligonucleotides are usually at a temperature of 0° C. to 5° C. below the Tm of the oligonucleotide in 6×SSC, 0.1% SDS.

The comparison of identity and calculation of homology of base sequences are herein calculated using BLAST (sequence analyzing tool) with the default parameters.

As used herein, the term "expression" of a gene, a polynucleotide, a polypeptide, or the like, indicates that the gene or the like is affected by a predetermined action in vivo to be changed into another form. Preferably, the term "expression" indicates that genes, polynucleotides, or the like are transcribed and translated into polypeptides. In one embodiment of the "expression", genes may be transcribed into mRNA. More preferably, these polypeptides may have post-translational processing modifications.

As used herein, the term "amino acid" may be naturally occurring or non-naturally occurring. The term "derivative amino acid" or "amino acid analog" refers to an amino acid which is different from a naturally-occurring amino acid but has a function similar to that of the naturally-occurring amino acid. Such a derivative amino acid and amino acid analog are well known in the art. The term "naturally-occurring amino acid" refers to an L-isomer of a naturally-occurring amino acid. The naturally-occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine, and lysine. Unless otherwise indicated, all amino acids as used herein are L-isomers. The term "nonnaturally-occurring amino acid" refers to an amino acid which is ordinarily not found in protein in nature. Examples of nonnaturally-occurring amino acids include D- or L-isomers of norleucine, para-nitrophenylalanine, homophenylalanine, para-fluorophenylalanine, 3-amino-2-benzyl propionic acid and homoarginine, and D-phenylalanine. The term "amino acid analog" refers to a molecule having a physical property and/or function similar to that of amino acids, but is not an amino acid. Examples of amino acid analogs include, for example, ethionine, canavanine, 2-methylglutamine, and the like. An amino acid mimic refers to a compound which has a structure different from that of the general chemical structure of amino acids but which functions in a manner similar to that of naturally-occurring amino acids.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the term "corresponding" amino acid refers to an amino acid in a given protein or polypeptide molecule, which has, or is anticipated to have, a function similar to that of a predetermined amino acid in a protein or polypeptide as a reference for comparison. Particularly, in the case of enzyme molecules, the term refers to an amino acid which is present at a similar position in an active site and similarly contributes to catalytic activity.

As used herein, the term "nucleotide" may either be naturally-occurring or nonnaturally-occurring. The term "nucleotide derivative" or "nucleotide analog" refers to a nucleotide which is different from naturally-occurring nucleotides and has a function similar to that of the original nucleotide. Such nucleotide derivatives and nucleotide analogs are well known in the art. Examples of such nucleotide derivatives and nucleotide analogs include, but are not limited to, phosphorothioate, phosphoramidate, methylphosphonate, chiral-methylphosphonate, 2-O-methyl ribonucleotide, and peptide-nucleic acid (PNA).

As used herein, the term "fragment" with respect to a polypeptide or a polynucleotide refer to a polypeptide or polynucleotide having a sequence length ranging from 1 to n−1 with respect to the full length of the reference polypeptide or polynucleotide (of length n). The length of the fragment can be appropriately changed depending on the purpose. For example, in the case of polypeptides, the lower limit of the length of the fragment includes 3, 4, 5, 6, 7, 8, 9, 10, 15, 20, 25, 30, 40, 50 or more amino acids. Lengths represented by integers which are not herein specified (e.g., 11 and the like) may be appropriate as a lower limit. For example, in the case of polynucleotides, the lower limit of the length of the fragment includes 5, 6, 7, 8, 9, 10, 15, 20, 25, 30, 40, 50, 75, 100 or more nucleotides. Lengths represented by integers which are not herein specified (e.g., 11 and the like) may be appropriate as a lower limit.

In plants, the targeting of a desired protein to mitochondria can be achieved by, for example, operatively linking a nucleic acid encoding a mitochondrial targeting sequence derived from any mitochondrial protein, such as plant mitochondrial proteins, with a nucleic acid coding a desired protein.

As used herein, the term "mitochondrial targeting sequence" refers to a sequence which transports a protein operatively linked therewith to mitochondria. As used herein, the term "mitochondrial targeting ability" refers to ability to transport a protein operatively linked therewith to mitochondria. Examples of the mitochondrial targeting sequence includes, but are not limited to, a mitochondrial ribosome protein, and a mitochondrial targeting sequence of ATP synthase subunit. Examples of a mitochondrial ribosome protein as a source of a mitochondrial targeting sequence of the present invention include, but are not limited to, a rice RPS10 protein (SEQ ID NO. 2) (FIG. 1), RPS14 protein (SEQ ID NO. 4) (FIG. 2) and RPS11 protein, and mitochondrial targeting sequences derived from ATPase β-subunit protein and ATPase γ-subunit protein. As a mitochondrial targeting sequence for RPS10 protein, for example, a polypeptide containing a sequence of amino acids 1 to 56 can be used. Variant polypeptides of these mitochondrial targeting sequences which have one or several amino acid substitutions, additions or deletions and have mitochondrial targeting ability, can also be used in the present invention. Fragments of these mitochondrial targeting sequences can also be used. Nucleic acids hybridizable to the nucleic acids coding these mitochondrial targeting sequences under stringent conditions can also be used. These amino acid sequences and/or nucleic acid sequences which have one or several deletions, additions or substitutions can also be used. Sequences having homology with the sequences can also be used. As a mitochondrial targeting sequence for RPS14 protein, for example, a polypeptide containing a sequence of amino acids 1 to 48 can be used. Variant polypeptides of these mitochondrial targeting sequences which have one or several amino acid substitutions, additions or deletions and have mitochondrial targeting ability, can also be used in the present invention. Fragments of these mitochondrial targeting sequences can also be used. Nucleic acids hybridizable to the nucleic acids encoding these mitochondrial targeting sequences under stringent conditions can also be used. Amino acid sequences and/or nucleic acid sequences which have one or several deletions, additions or substitutions in these amino acid sequences and/or nucleic acid sequences can also be used. Sequences having homology with the sequences can also be used.

In plants, the targeting of a desired protein to Golgi apparatus can be achieved by, for example, operatively linking a nucleic acid encoding a Golgi apparatus targeting sequence derived from any plant Golgi apparatus protein with a nucleic acid coding a desired protein.

As used herein, the term "Golgi apparatus targeting sequence" refers to a sequence which transports a protein operatively linked therewith to Golgi apparatus. As used herein, the term "Golgi apparatus targeting ability" refers to ability to transport a protein operatively linked therewith to Golgi apparatus. Examples of the Golgi apparatus targeting sequence includes, but are not limited to, a Golgi apparatus targeting sequence of N-acetylglucosaminyl transferase protein. Examples of a Golgi apparatus protein as a source of a Golgi apparatus targeting sequence of the present invention include, but are not limited to, a Golgi apparatus targeting sequence derived from tobacco N-acetylglucosaminyl transferase protein (SEQ ID NO. 8) (FIG. 3). As a Golgi apparatus targeting sequence for tobacco N-acetylglucosaminyl transferase protein, for example, a polypeptide containing a sequence of amino acids 1 to 77 can be used. Variant polypeptides of these Golgi apparatus targeting sequences which have one or several amino acid substitutions, additions or deletions and have Golgi apparatus targeting ability, can also be used in the present invention. Fragments of these Golgi apparatus targeting sequences can also be used. Nucleic acids hybridizable to the nucleic acids encoding these Golgi apparatus targeting sequences under stringent conditions can also be used. Amino acid sequences and/or nucleic acid sequences which have one or several deletions, additions or substitutions in these amino acid sequences and/or nucleic acid sequences can also be used. Sequences having homology with the sequences can also be used.

Examples of decaprenyl diphosphate synthase that can synthesize 10 units of side chain of ubiquinone, is derived from a bacterium include, but are not limited to, an enzyme encoded by a gene derived from *Gluconobacter suboxydans* (SEQ ID NO. 5). Variant polypeptides of these decaprenyl diphosphate synthases whose amino acid sequence has one or several amino acid substitutions, additions or deletions and which has enzyme activity, can be used in the present invention. Further, fragments of the amino acid sequences of these enzymes can be used. Nucleic acids hybridizable to the nucleic acids coding these enzyme proteins under stringent conditions can also be used. Amino acid sequences and/or nucleic acid sequences which have one or several deletions, additions or substitutions in these amino acid sequences and/or nucleic acid sequences can also be used. Sequences having homology with the sequences can also be used.

As used herein, the terms "transformation" and "gene introduction" are used interchangeably. "Transformation" indicates that an exogenous nucleic acid including a gene is introduced into plant cells or plant tissue, resulting in a change in the genotype of the plant cells or the plant tissue.

As used herein, the term "transformant" refers to the whole or a part of an organism, such as a cell which is produced by transformation of a host cell. Transformants may be referred to as transformed cells, transformed tissue, transformed hosts, transformant calluses, transformant plants or the like, depending on the object to be transformed. As used herein, transformants encompass all of these forms, though a particular form may be intended in a particular context.

As used herein, the term "transgenic plant" and "recombinant plant" refers to a plant into which a specific gene is introduced.

Plants can be herein cultivated by any known method in the art. Methods of cultivating plants are illustrated in, for example, "Moderu-shokubutsu-no-Jikken-Purotokoru, Ine. Shiroinunazuna-hen: Saibo-kogaku Bessatsu-shokubutsu-saibo-kogakusirizu 4; Ine-no-saibaiho [Experimental Protocol for Model Plants For Rice and *Arabidopsis thaliana*: Cell Engineering, Special Issue, Plant Cellular Engineering Series 4; Rice Cultivating Methods]" (Kazutoshi Okuno) pp. 28-32, and "Arabidopushisu-no-saibaiho [Cultivating Methods for *Arabidopsis*]" (Yasuo Tanba) pp. 33-40 (Supervised by Ko Shimamoto and Kiyotaka Okada), which can be easily performed by those skilled in the art. Thus, it is not necessary to describe these method in detail.

Any host plant cells which can express a polypeptide (e.g., decaprenyl diphosphate synthase) maintaining the physiological activity of a foreign gene can be used to obtain a transformant. Various host plant cells which have been conventionally used for genetic engineering can be used. Examples of the host plants include rice, cucumber, sugarcane, oat, maize, wheat, barley, buckwheat, Job's-tears, wild oat, barnyard grass, soybean, almond, pistachio, peanut, hazel, walnut, cashew, sesame, billion-dollar grass, banana, tomato, potato, sweet potato, alga, chlorella, sugarcane, and the like. A preferable plant cell is a plant which produces ubiquinone-9, but not ubiquinone-10. Examples of such a plant include, but are not limited to, wheat, barley, buckwheat, Job's-tears, wild oat, and barnyard glass. Further, a plant which mainly produces ubiquinone-9 with a relatively small amount of ubiquinone-10, and a plant which mainly produces ubiquinone-10 with a relatively small amount of ubiquinone-9, are encompassed by the present invention. This is because the production of ubiquinone-10 can be enhanced by supplying foreign decaprenyl diphosphate synthase. Examples of such a plant include, but are not limited to, onion, pimento, soybean, almond, pistachio, peanut, hazel, walnut, cashew, and sesame.

A polypeptide derived from a cell obtained in the present invention may have one or more amino acid substitutions, additions and/or deletions in its amino acid sequence or one or more sugar chain substitutions, additions and/or deletions as long as it has a function substantially similar to its naturally-occurring polypeptide.

A certain amino acid may be substituted with another amino acid in a protein structure, such as a binding site for a ligand molecule, without a significant reduction or elimination of interactive binding capability. The biological function of a certain protein is determined by the interaction capability and properties of the protein. Therefore, even if substitution of a particular amino acid is performed in an amino acid sequence (or at the DNA coding sequence level), a protein may maintain its original properties after the substitution. Therefore, peptides disclosed herein or DNA encoding the peptides may be modified in various manners without clearly impairing their biological usefulness.

When the above-described modifications are designed, the hydrophobicity indices of amino acids may be taken into consideration. The hydrophobic amino acid indices play an important role in providing a protein with an interactive biological function, which is generally recognized in the art (Kyte, J. and Doolittle, R. F., J. Mol. Biol. 157 (1): 105-132, 1982). The hydrophobic property of an amino acid contributes to the secondary structure of a protein and then regulates interactions between the protein and other molecules (e.g., enzymes, substrates, receptors, DNA, antibodies, antigens, etc.). Each amino acid is given a hydrophobicity index based on the hydrophobicity and charge properties thereof as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

It is well known that if a given amino acid is substituted with another amino acid having a similar hydrophobicity index, the resultant protein may still have a biological function similar to that of the original protein (e.g., a protein having an equivalent ligand binding capability). For such an amino acid substitution, the hydrophobicity index is preferably within ±2, more preferably within ±1, and even more preferably within ±0.5. It is understood in the art that such an amino acid substitution based on hydrophobicity is efficient. As described in U.S. Pat. No. 4,554,101, amino acid residues are given the following hydrophilicity indices: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5);cysteine (−1.0);methionine (−1.3); valine (−1.5); leucine (−1.8); isoleucine (−1.8); tyrosine (−2.3); phenylalanine (−2.5); and tryptophan (−3.4). It is understood that an amino acid may be substituted with another amino acid which has a similar hydrophilicity index and can still provide a biological equivalent protein/polypeptide. For such an amino acid substitution, the hydrophilicity index is preferably within ±2, more preferably ±1, and even more preferably ±0.5.

The term "conservative substitution" as used herein refers to amino acid substitution in which a substituted amino acid and a substituting amino acid have similar hydrophilicity indices or/and hydrophobicity indices. Examples of the conservative substitution include, but are not limited to, substitutions within each of the following residue pairs: arginine and lysine; glutamic acid and aspartic acid; serine and threonine; glutamine and asparagine; and valine, leucine, and isoleucine, which are well known to those skilled in the art.

As used herein, the term "variant" refers to a substance, such as a polypeptide, polynucleotide, or the like, which differs partially from the original substance. Examples of such a variant include a substitution variant, an addition variant, a deletion variant, a truncated variant, an allelic variant, and the like. The term "allele" as used herein refers to a genetic variant located at a locus identical to a corresponding gene, where the two genes are distinguished from each other. Therefore, the term "allelic variant" as used herein refers to a variant which has an allelic relationship with a given gene. The term "species homolog" or "homolog" as used herein refers to one that has an amino acid or nucleotide homology with a given gene in a given species (preferably at least 60% homology, more preferably at least 80%, at least 85%, at least 90%, and at least 95% homology). A method for obtaining such a species homolog is clearly understood from the description of the present specification. The term "orthologs" (also called orthologous genes) refers to genes in different species derived from a common ancestry (due to speciation). For example, in the case of the hemoglobin gene family having multigene structure, human and mouse α-hemoglobin genes are orthologs, while the human α-hemoglobin gene and the human β-hemoglobin gene are paralogs (genes arising from gene duplication). Orthologs are useful for estimation of molecular phylogenetic trees. Therefore, orthologs and paralogs of the present invention may be useful in the present invention.

As used herein, the term "conservative (or conservatively modified) variant" applies to both amino acid and nucleic acid sequences. With respect to particular nucleic acid sequences, conservatively modified variants refer to those nucleic acids which encode identical or essentially identical amino acid sequences. When the nucleic acid does not encode amino acid sequence, the conservative nucleic acid sequence means the substantially identical sequence. Because of the degeneracy of the genetic code, a large number of functionally identical nucleic acids encode any given protein. For example, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" which represent one species of conservatively modified variation. Every nucleic acid sequence herein which encodes a polypeptide also describes every possible silent variation of the nucleic acid. Those skilled in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence. Preferably, such modification may be performed while avoiding substitution of cysteine which is an amino acid capable of largely affecting the higher-order structure of a polypeptide.

In order to prepare functionally equivalent polypeptides, amino acid additions, deletions, or modifications can be performed in addition to amino acid substitutions. Amino acid substitution(s) refers to the replacement of at least one amino acid of an original peptide with different amino acids, such as the replacement of 1 to 10 amino acids, preferably 1 to 5 amino acids, and more preferably 1 to 3 amino acids with different amino acids. Amino acid addition(s) refers to the addition of at least one amino acid to an original peptide chain, such as the addition of 1 to 10 amino acids, preferably 1 to 5 amino acids, and more preferably 1 to 3 amino acids to an original peptide chain. Amino acid deletion(s) refers to the deletion of at least one amino acid, such as the deletion of 1 to 10 amino acids, preferably 1 to 5 amino acids, and more preferably 1 to 3 amino acids, from an original peptide. Amino acid modification includes, but is not limited to, amidation, carboxylation, sulfation, halogenation, alkylation, glycosylation, phosphorylation, hydroxylation, acylation (e.g., acetylation), and the like. Amino acids to be substituted or added may be naturally-occurring or non-naturally-occurring amino acids, or amino acid analogs. Naturally-occurring amino acids are preferred.

The above-described nucleic acid encoding a protein can be obtained by a well-known PCR method, or by a chemical synthesis. This method may be combined with, for example, site-directed mutagenesis, hybridization, or the like.

As used herein, the term "substitution, addition or deletion" for a polypeptide or a polynucleotide refers to the substitution, addition or deletion of an amino acid or its substitute, or a nucleotide or its substitute with respect to the original polypeptide or polynucleotide. This is achieved by techniques well known in the art, including a site-directed mutagenesis technique and the like. A polypeptide or a polynucleotide may have any number (>0) of substitutions, additions, or deletions. The number can be as large as a variant having such a number of substitutions, additions or deletions maintains an intended function (e.g., a cancer marker, a disease marker, etc.). For example, such a number may be one or several, and preferably within 20% or 10% of the full length, or no more than 100, no more than 50, no more than 25, or the like.

General molecular biological techniques which may be used in the present invention can be easily performed by those skilled in the art with reference to, for example, Ausubel F. A. et al. (1988), Current Protocols in Molecular Biology, Wiley, New York, N.Y.; Sambrook J. et al. (1987) Molecular Cloning: A Laboratory Manual, 2nd Ed., Cold Spring Harbor Laboratory Press, Cold Spring Harbor, N.Y.

When a gene is mentioned herein, the term "vector" refers to an agent which transfers a polynucleotide sequence of interest to a target cell. Such a vector is, for example, capable of self-replication in a host cell and contains a promoter at a site suitable for transcription of a polynucleotide of the present invention.

As used herein, the term "expression vector" refers to a nucleic acid sequence wherein comprising a structural gene and a promoter for regulating expression thereof, and in addition, various regulatory elements linked in a state that allows them to operate within host cells. The regulatory element may include, preferably, terminators, selectable markers such as drug-resistance genes, and enhancers. It is well known to those skilled in the art that the types of an expression vector and a regulatory element used may vary depending on the host plant cell.

As used herein, the term "recombinant vector" refers to a vector which can transfer a polynucleotide sequence of interest to a target cell. Examples of such a vector include vectors which are capable of self replication in a host eukaryotic cell and contain a promoter at a site suitable for transcription of a polynucleotide of the present invention.

Examples of "recombinant vectors" for plant cells include Ti plasmid, Ri plasmid, tobacco mosaic virus vector, Gemini virus vector, and the like. Note that these vectors may not be used when a direct introduction technique, such as particle gun, electroporation or the like, is used.

As used herein, the term "promoter" refers to a DNA region which determines the initiation site of transcription of a gene and in which directly regulates the frequency of transcription. Transcription is started by RNA polymerase binding to a promoter. A putative promoter region is usually located upstream of a structural gene, but depending on the structural gene, i.e., a putative promoter region may be located downstream of a structural gene.

As used herein, the term "terminator" refers to a sequence which is located downstream of a protein-encoding region of a gene and which is involved in the termination of transcription when DNA is transcribed into mRNA, and the addition of a poly-A sequence. It is known that a terminator contributes to the stability of mRNA, and has an influence on the amount of gene expression. Examples of such a terminator include, but are not limited to, a CaMV35S terminator, a terminator for the nopaline synthase gene (Tnos), and a terminator for the tobacco PR1a gene. As used herein, the term "promoter" refers to a DNA region which determines the initiation site of transcription of a gene and which directly regulates the frequency of transcription. Transcription is started by RNA polymerase binding to a promoter. A promoter region is usually located within about 2 kbp upstream of the first exon of a putative protein coding region. Therefore, it is possible to estimate a promoter region by predicting a protein coding region in a genomic base sequence using DNA analysis software. A putative promoter region is usually located upstream of a structural gene. Preferably, a putative promoter region is located within about 2 kbp upstream of the translation initiation site of the first exon.

As used herein, the term "site specificity" in relation to gene expression, generally refers to the expression specificity of a gene with respect to a site (e.g., in the case of plants: roots, stems, trunks, leaves, flowers, seeds, embryo buds, embryos, fruits, and the like) within an organism (e.g., plants). The term "time specificity" refers to the expression specificity of a gene with respect to a developmental stage (e.g., in the case of plants, growth stage, and the number of days of a seedling after germination) of an organism (e.g., plants). Such specificity can be introduced into a desired organism using an appropriately selected promoter.

As used herein, the term "constitutive" for expression of a promoter of the present invention refers to a character of the promoter that the promoter is expressed in a substantially constant amount in all tissues of an organism no matter whether the growth stage of the organism is a juvenile phase or a mature phase. Specifically, when Northern blotting analysis is performed under the same conditions as those described in examples of the present specification, expression is considered to be constitutive according to the definition of the present invention if substantially the same amount of expression is observed at the same or corresponding site at any time (e.g., two or more time points (e.g., day 5 and day 15)), for example. Constitutive promoters are considered to play a role in maintaining the homeostasis of organisms in a normal growth environment. As used herein, the term "stress responsive" for promoter expression refers to a character of a promoter that when at least one stress is experienced by an organism, the expression amount of the promoter is changed. Particularly, a character of increasing an expression amount is referred to as "stress inducible". A character of reducing an expression amount is referred to as "stress suppressible". "Stress suppressible" expression is based on the premise that expression is observed in a normal situation. Therefore, this concept overlaps with "constitutive" expression. These characters can be determined by extracting RNA from any portion of an organism and analyzing the expression amount of the RNA by Northern blotting or quantitating expressed proteins by Western blotting. When a plant or a portion thereof (particular cells, tissue, or the like) is transformed with a vector comprising a stress inducible promoter and a nucleic acid encoding a polypeptide of the present invention, a stimulator having activity of inducing the promoter can be used to cause the particular gene to be expressed under predetermined conditions.

An "enhancer" may be used so as to enhance the expression efficiency of a gene of interest. As such an enhancer which is used in plants, an enhancer region containing an upstream sequence within the CaMV35S promoter is one example. One or more enhancers may be used, or no enhancer may be used.

As used herein, the term "operatively linked" indicates that a desired sequence is located such that expression (operation) thereof is under control of a transcription and translation regulatory sequence (e.g., a promoter, an enhancer, and the like) or a translation regulatory sequence. In order for a promoter to be operatively linked to a gene, typically, the promoter is located immediately upstream of the gene. There may be an intervening sequence between a promoter and a structural gene. In other words, a promoter is not necessarily adjacent to a structural gene. Note that, a targeting sequence to organelles is located in the same frame as a gene encoding a protein.

The presence of an introduced gene may be confirmed using a PCR technique, a Southern blotting technique or the like. Expression of an introduced gene may be detected using a northern blotting technique or an RT-PCR technique. Expression of a protein (gene product) may be optionally confirmed using, for example, a western blotting technique.

(General Techniques Used Herein)

Techniques used herein are within the technical scope of the present invention unless otherwise specified. These techniques are commonly used in the fields of sugar chain science, microfluidics, micromachining, organic chemistry, biochemistry, genetic engineering, molecular biology, microbiology, genetics, and their relevant fields. The techniques are well described in documents described below and the documents mentioned herein elsewhere.

Molecular biological techniques, biochemical techniques, microbiological techniques and sugar chain scientific techniques used herein are well known and commonly used in the art, and are described in, for example, Maniatis, T. et al. (1989), Molecular Cloning: A Laboratory Manual, Cold Spring Harbor and its 3rd Ed. (2001); Ausubel, F. M., et al. eds, Current Protocols in Molecular Biology, John Wiley & Sons Inc., NY, 10158 (2000); Innis, M. A. (1990), PCR Protocols: A Guide to Methods and Applications, Academic Press; Innis, M. A. et al. (1995), PCR Strategies, Academic Press; Sninsky, J. J. et al. (1999), PCR Applications: Protocols for Functional Genomics, Academic Press; Gait, M. J. (1985), Oligonucleotide Synthesis: A Practical Approach, IRL Press; Gait, M. J. (1990), Oligonucleotide Synthesis: A Practical Approach, IRL Press; Eckstein, F. (1991), Oligonucleotides and Analogues: A Practical Approach, IRL Press; Adams, R. L. et al. (1992), The Biochemistry of the Nucleic Acids, Chapman & Hall; Shabarova, Z. et al. (1994), Advanced Organic Chemistry of Nucleic Acids, Weinheim; Blackburn, G. M. et al. (1996), Nucleic Acids in Chemistry and Biology, Oxford University Press; Hermanson, G. T. (1996), Bioconjugate Techniques, Academic Press; Method in Enzymology 230, 242, 247, Academic Press, 1994; Special issue, Jikken Igaku [Experimental Medicine] "Idenshi Donyu & Hatsugenkaiseki Jikkenho [Experimental Method for Gene introduction & Expression Analysis]", Yodo-sha, 1997; and the like. Relevant portions (or possibly the entirety) of each of these publications are herein incorporated by reference.

(Food Additives)

Ubiquinone-10 of the present invention can be used as a food additive (dietary food). Ubiquinone-10 as a food additive is expected to have a beneficial effect for antioxidant substances, skin aging, immunodeficiency, heart disease, periodontal disease, chronic fatigue syndrome, retrograde brain, neural motor function disorder, diabetes, stroke, arteriosclerosis, cancer, hypertension, hypotension, cerebral infarction, allergic disease, and the like. Ubiquinone-10 is also expected to have an action to enhance the ability of a heart, and specifically, have a beneficial effect for congestive cardiac failure, and in addition, palpitation/shortness of breath, foot or face swelling, oversensitivity to cold temperatures and the like.

For a healthy person, ubiquinone-10 as a food additive is normally given in a dose of about 30 mg/day. For a patient with heart disease, the dose is typically about 100 mg/day or more. However, the dose may vary depending on the conditions of each person who takes the food additive.

When ubiquinone-10 is used as a food additive, the ubiquinone-10 may be dissolved in, for example, soybean oil or the like, since purified ubiquinone-10 is fat-soluble. Alternatively, powdered ubiquinone-10 may be enclosed in a capsule. Ubiquinone-10 may also be added to a drink. When the ubiquinone-10 of the present invention is used as a food additive, a vitamin, such as vitamin E, may be blended thereinto as required.

For example, the ubiquinone-10 food additive can be formulated in accordance with a formula below. However, the present invention is not limited to this. For example, ubiquinone-10 can be blended with DHA-containing purified fish oil, soy bean lecithin, bees wax, and vitamin E (302% with respect to the recommended dietary requirements), and the resultant mixture can be encapsulated using gelatin, glycerin and caramel coloring matter into a tablet, which can be used as a food additive.

Alternatively, the ubiquinone-10 food additive can be formulated in accordance with a formula below. However, the present invention is not limited to this. For example, ubiquinone-10 can be blended with lactose, an emulsifier, soy bean extract, hawthorn extract, a gelling agent, micro particle silicon dioxide, niacinamide, vitamin E, glycerin, a colorant (titanium dioxide), vitamin B6, vitamin B2, carotene, and gelatin.

(Formula)

The invention also provides methods of treatment and/or prevention diseases or disorders (e.g., heart disease) by administration to a subject of an effective amount of a therapeutic agent. By therapeutic agent, it is meant a composition of the present invention in combination with a pharmaceutically acceptable carrier type (e. g., a sterile carrier).

The therapeutic agent will be formulated and dosed in a fashion consistent with Good Medical Practice (GMP), taking into account the clinical condition of the individual patient (especially the side effects of treatment with the therapeutic agent alone), the site of delivery, the method of administration, the scheduling of administration, and other factors known to those skilled in the art. The "effective amount" for purposes herein is thus determined by such considerations.

The therapeutic agent can be administered orally. The term "pharmaceutically acceptable carrier" refers to a non-toxic solid, semisolid or liquid filler, diluents, encapsulating material or formulation auxiliary of any type.

Generally, formulations are prepared by contacting the therapeutic agent uniformly and closely with liquid carriers or finely divided solid carriers or both. Then, if necessary, the product is shaped into the desired formulation. Examples of such carrier vehicles include non-aqueous vehicles, such as soybean oil and ethyl oleate, which are useful herein.

The present invention also provides a pharmaceutical pack or kit comprising one or more containers filled with one or more of the ingredients of the therapeutic agent of the present invention. Associated with such container (s), can be a notice in the form prescribed by a governmental agency regulating the manufacture, use or sale of pharmaceuticals or biological products, which notice reflects approval by the agency of government regarding manufacture, use or sale for human administration. In addition, the therapeutic agent may be employed in conjunction with other therapeutic compounds.

The therapeutic agent of the present invention may be administered alone or in combination with other therapeutic agents. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e. g., as through separate intravenous lines into the same individual. Administration "in combination" further includes the separate administration of one of the compounds or agents given first, followed by the second.

(Intake of Ubiquinone-10)

Ubiquinone-10 of the present invention can be used for the prevention, treatment and prognosis of various diseases and conditions.

Examples of the diseases and conditions to which Ubiquinone-10 of the present invention can be applied include Alzheimer's disease, Parkinson's disease, and Huntington's disease. The reason why ubiquinone-10 is considered to be able to be used for prevention and treatment of these diseases is the following. Most of the diseases relevant to the brain are considered to be caused by active oxygen putting damage on nervous tissue. Ubiquinone-10 plays a role in protecting mitochondria in brain cells, thus considered to act to prevent brain diseases.

Ubiquinone-10 of the present invention can be used to prevent and ameliorate cancer. It is known that cancer patients have a very low ubiquinone-10 level. Therefore, a number of tests have been reported in which ubiquinone-10 is applied for therapy of cancer. There have been some reports that administration of ubiquinone-10 stopped progression of cancer and ameliorated its condition. In a report among them, tumor was completely eliminated after two months of administration of ubiquinone-10 in a dose of as large as 390 mg per day. Ubiquinone-10 is also used in actual clinical situations.

Ubiquinone-10 of the present invention can also be used as an anti-aging agent. This is because ubiquinone-10 is a potent antioxidant substance, and therefore, is expected to prevent oxidation of cells, thereby providing an anti-aging effect. Actually, there has been a report that 30% of mice into which ubiquinone-10 was administered lived longer by about two months than mice without ubiquinone-10 administration.

Ubiquinone-10 of the present invention can be applied to relax wrinkles. Actually, it has been confirmed that wrinkles are reduced by applying ubiquinone-10 on skin.

Ubiquinone-10 of the present invention can be applied to reduce obesity. It is known that ubiquinone-10 increases the rate of metabolism, which contributes to a reduction in weight. It is known that, when a portion of obese patients who lack ubiquinone-10 in their bodies are supplemented with ubiquinone-10, their calorie combustion rates are increased. There has been a report of an experiment in which, when obese patients took 100 mg of ubiquinone-10 for 8 to 9 weeks, some of them who lacked ubiquinone-10 lost in weight an amount two times or more that of the others who had a normal ubiquinone-10 level.

Ubiquinone-10 of the present invention can also be used to ameliorate chronic fatigue syndrome. The symptoms of chronic fatigue syndrome include non-stop fatigue, insomnia, low-grade fever, migraine, and the like. These symptoms are considered to be caused by occurrence of a certain failure in a system which produces energy in mitochondria. Actually, there has been a report that administration of ubiquinone-10 improved exercise tolerance and reduced a time required for restoration.

Further, ubiquinone-10 of the present invention is considered to enhance the immune system, ameliorate gingivitis and periodontal disease, delay the onset of AIDS, prevent arteriosclerosis, and ameliorate diabetes.

The intake amount of a ubiquinone-10 food additive can be adjusted with reference to the following indexes for various diseases and conditions.

By blood collection, it can be determined whether or not a patient is deficient in ubiquinone-10. Generally, the average plasma ubiquinone-10 level is 0.8 μg/ml in healthy persons. If a person has a plasma ubiquinone-10 level of less than that value, he or she may be supplemented with ubiquinone-10. An appropriate intake dose varies depending on the form (capsule, oil-based soft capsule, etc.) when taken as healthy food. The dose also varies depending on the deficiency level, dietary habit, various other factors, symptom, purpose or the like of a patient. The intake amount of ubiquinone-10 as a food additive is generally about 30 to 300 mg/day. For example, the guidance intake amount of ubiquinone-10 is about 30 to about 60 mg/day for general health maintenance and aging prevention; about 60 to about 90 mg/day for improvement of stamina and strength; about 60 to about 150 mg in the case of a specific disease and symptom; and about 90 mg or more in the case of excessive exercise, but are not limited to these values.

In administration to those who have specific diseases and/or conditions, the guideline administration dose of ubiquinone-10 is 30 mg/day for bronchial asthma; 100 mg/day for cirrhosis; 100 mg/day for diabetes; 100 mg/day for periodontal disease; 300 mg/day for fatigue; 300 mg/day for high cholesterol level; 75 to 360 mg/day for hypertension; 90 to 390 mg/day for lung cancer; 75 to 600 mg/day for heart disease; and 400 to 800 mg/day for Parkinson's disease. Note that a treatment period required for observation of a change and intervals at which a response occurs after treatment, may vary depending on the desired effect.

(Transformation)

Transformation is generally carried out by a method of directly introducing a gene into plants (direct gene introduction method), or a method of indirectly introducing a gene into plants (indirect gene introduction method).

To date, as an indirect gene introduction method, a method using *Agrobacterium* is widely used. For example, full mature seeds of rice are cultured; and after three weeks, callus obtained is infected with *Agrobacterium* (see Hiei et al., Plant Journal, 6:271-282, 1994), or seeds are infected with *Agrobacterium* 4-5 days after germination in order to quickly obtain transformants (Tanaka et al., Japanese Patent No. 3141084).

As a direct gene introduction method, a particle gun method (see Christou, P. et al., Bio/Technology, 9:957-962, 1991), a polyethylene glycol method (Datta, S. K. et al., Bio/Technology, 8:736-740, 1990), an electroporation method (see Shimamoto, K. et al., Nature, 338:274-276, 1989), and the like are used for production of transformants. Electroporation refers to a method of introducing a gene into cells, in which a small hole is physically opened on a plant cell by applying direct current high voltage pulses, and a gene is introduced into the cell through the hole. In the case of gene introduction into wheat, an immature embryo is used (see J. T. Weeks et al., Plant. Physiol., 102:1077-1084, 1993).

(Site-Specific Production of Ubiquinone-10)

Hereinafter, the present invention will be described by way of examples. Examples below are provided only for purposes of illustration. Therefore, the scope of the present invention is not limited to the above-described explanation or the examples below, except as by the appended claims.

EXAMPLES

Example 1

Construction of a Decaprenyl Diphosphate Synthase Gene (ddsA) Linked with a Mitochondrial Targeting Sequence or a Golgi Apparatus Targeting Sequence A ddsA gene having a nucleic acid sequence (SEQ ID NO. 5) was linked with a mitochondrial targeting sequence or a Golgi apparatus targeting sequence to construct plasmids. As the mitochondrial targeting sequence, S14 (Kubo et al., Plant Science 164 (2003) 1047-1055; corresponding to amino acid residues 1 to 48 of SEQ ID NO. 4) which is a mitochondrial targeting sequence derived from RPS14 (SEQ ID NO. 4), was used. As the Golgi apparatus targeting sequence, CTS (Essl et al., FEBS letters, 453 (1999) 169 to 173; amino acids 1 to 77 of SEQ ID NO. 8) which is a Golgi apparatus targeting signal located at the N terminus of tobacco N-acetylglucosaminyl transferase I (GnT1) (SEQ ID NO. 8), was used. These targeting sequences were operatively linked with a *Gluconobacter suboxydans*-derived decaprenyl diphosphate synthase gene (ddsA) (Okada et al., Eur. J. Biochem, 255, 52-59 (1998)), and the resultant sequences were each linked between a CaMV35S promoter (constitutive promoter) and a NOS terminator to construct a pUS14 ddsA plasmid and a pUCT ddsA plasmid. HindIII/EcoRI fragments of each plasmid were linked with multiple cloning sites of a binary vector pCAMBIA1301. A schematic diagram of each plasmid thus constructed is shown in FIG. 6.

Example 2

Confirmation of Expression of the ddsA Gene

Rice was transformed using the plasmids produced in Example 1. Specifically, *Agrobacterium* (*Agrobacterium tumefaciens*) line EHA105 was transformed by electroporation. The resultant *Agrobacterium* was used in accordance with a transformation technique described in WO 01/06844 to transform the plant. The transformed rice was screened in medium containing hygromycin (50 mg/L). It was confirmed that the ddsA gene was introduced into the plant cells, by PCR amplification experiments or Southern hybridization described below (data not shown).

Rice genomic DNA (4 µg) was digested with HindIII, followed by 0.9% agarose electrophoresis. The resultant fragments were blotted onto Hybond-N+membrane (Amarsham Pharmacia) due to capillary action (Sambrook, Fritsch and Maniatis, Molecular Cloning: A Laboratory Manual (2nd Edition, Cold Spring Harbor Laboratory, 1989)). A 0.3-kb fragment (a 5' portion of the coding region) of the ddsA gene was used as a probe. The probe was labeled in accordance with instructions of Roche (manufacturer). Hybridization and washing were performed in accordance with Sambrook (described above). The subsequent reactions were performed in accordance with the instructions of Roche. Final washing was performed using 0.1×SSC and 0.1% SDS at 68° C. As a result, a clone in which an intended plasmid was incorporated into chromosomal DNA was found. The clone was used in the subsequent experiments.

Example 3

Preparation of an Anti-*G. saboxydans* DDSA Antibody

The whole coding region of the ddsA gene was PCR-amplified and linked with pGEX4T-3 vector (Amersham Pharmacia), which was in turn used to transform *E. coli* JM109. Expression of a GST/DDSA fusion protein was induced by addition of 1-mM IPTG, followed by purification in accordance with an Asano et al. (Plant Cell (2002) 14, 619-628). The purified fusion protein was injected into a rabbit at intervals of two weeks (a total of 6 times). As a result, an anti-*G. saboxydans* DDSA antibody was confirmed in rabbit serum.

Example 4

Confirmation of Expression of DDSA Protein

A leaf of the transgenic plant was mixed with an extraction buffer solution (50 mM Tris-HCl, pH 6.8, 2% SDS, 6% 2-mercaptoethanol, 10% glycerol) having an amount eight times the weight of the leaf, followed by pulverization. The suspension was centrifuged at 12,000 rpm at 4° C. for 5 minutes, and thereafter, the supernatant was collected. The whole protein (10 µg) derived from each transformant was separated into individual proteins using 12.5% polyacrylamide gel, and the individual proteins were transferred onto Immobillon PVDF membrane (manufactured by Millopore).

Figure 7:
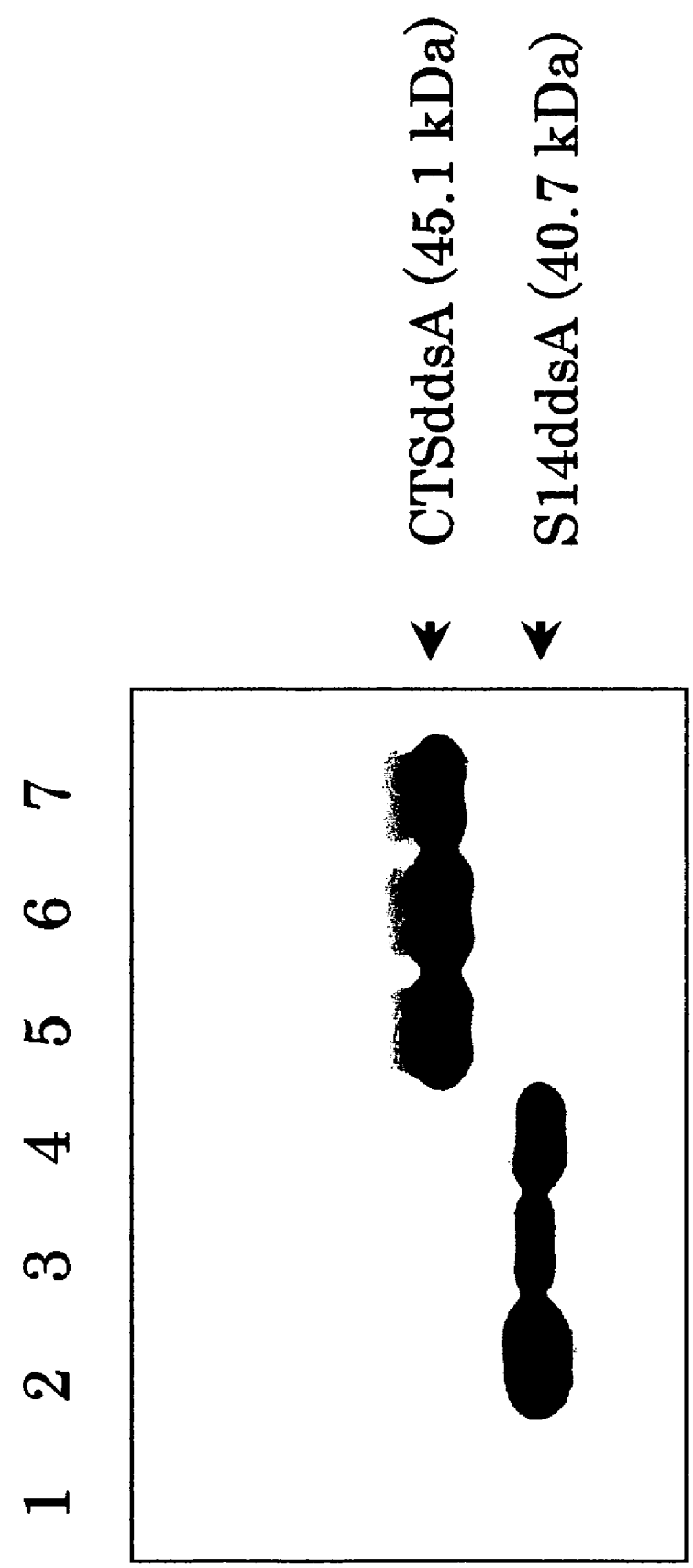
FIG. 7 shows a result of detection of expression of a fusion protein in Example 4.

The anti-DDSA antibody prepared in Example 3 was used to perform western blotting. In FIG. 7, a lane 1 indicates a protein derived from a non-transformed plant, while lanes 2 to 4 indicate a protein derived from a plant which was transformed using a plasmid which expresses DDSA fused with S14, and lanes 5 to 7 indicate a protein derived from a plant transformed using a plasmid which expresses DDSA fused with CTS. As shown in FIG. 7, expression of each fusion protein was confirmed.

The transformed plants which produce the S14-DDSA fusion protein were divided into four groups, depending on the expression level of the protein (±: very low expression level; L: low expression level; M: intermediate expression level; H: high expression level). The group ± included 15 individuals. The group L included 8 individuals. The group M included 9 individuals. The group H included 9 individuals.

Example 5

Extraction and Measurement of Ubiquinone

Ubiquinone was extracted in accordance with a slightly modified version of the method of Okuda et al. (described above). Rice leaf was pulverized in a mortar while pouring liquid nitrogen. The resultant rice leaf (1.0 g) was placed in a 15-ml tube. 3% $H_2SO_4$ (2 ml) was added to the tube, followed by stirring with a Vortex mixer for several seconds. The cap of the tube was removed, and the tube is capped with aluminum foil. The tube was autoclaved at 120° C. for 30 minutes. Thereafter, 14% NaOH (4 ml) was added to the tube. Next, the tube was autoclaved at 120° C. for 15 minutes, immediately followed by cooling in ice water. Hexane:isopropanol (5:1) (3 ml) was added to the tube, followed by stirring with a Vortex mixer for one minute. The tube was centrifuged at 2000 rpm at room temperature for two minutes. The supernatant (1.5 ml) was aliquoted into a 2-ml tube, followed vacuum drying for 10 minutes while heating. The dried material was suspended in 20 µl of chloroform:methanol (2:1), and the suspension was spotted onto a TLC plate. A reference ubiquinone-10 (1 mg/ml) (5 µl) was spotted onto another plate.

TLC development was performed using 100% benzene for about 1 hour and 20 minutes. After ultraviolet irradiation, the spot which is in the same position as the reference ubiquinone-10 spot was cut off using a cutter and was placed in a 1.5-ml tube. Hexane (200 µl) and isopropanol (200 µl) were added to the tube, followed by stirring with a Vortex mixer for one minute. The tube was centrifuged at 13,000 rpm at room temperature for one minute. The resultant supernatant was transferred to a 1.5-ml tube, followed by vacuum drying for 10 minutes. The dried material was suspended in 200 µl of 100% degassed ethanol. The suspension was filtered using a filter to remove solid matter. The suspension was analyzed with HPLC. The HPLC analysis was performed using a C18 reverse phase column (YMC-Pack ODS-A; 150 mm×60 mm) where ethanol was a solvent (flow rate=1 ml/min, 275 nm).

Figure 8:
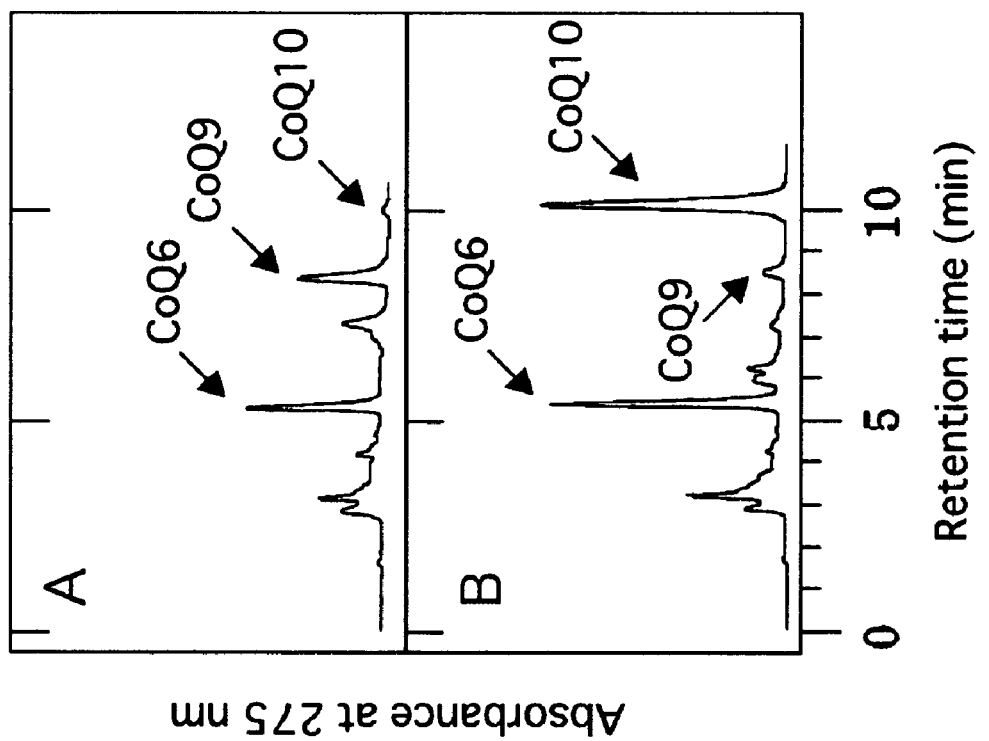
FIG. 8 shows amounts of produced ubiquinone-9 and ubiquinone-10 in a non-transformed plant (A), and a plant which expresses S14-DDSA (a fusion protein of S14 and DDSA) (B).

As a result, as shown in FIG. 8, it was observed that non-transformed rice (A in FIG. 8) contained a larger amount of ubiquinone-9 and a smaller amount of ubiquinone-10, while a transformed plant which expressed S14-DDSA (B in FIG. 8) contained substantially no ubiquinone-9 and a large amount of ubiquinone-10. As can be seen from this, by linking a mitochondrial targeting sequence with a decaprenyl diphosphate synthase gene and causing the resultant sequence to be expressed in plants, a large amount of ubiquinone-10 can be produced in plants. Note that ubiquinone-6 was added as an internal reference for measurement.

To confirm the molecular mass of each ubiquinone, we performed liquid chromatography-MS (LC-MS) using a LCT LC-MS system (Micromass) equipped with an atmospheric pressure chemical ionization (APCI) source [Inertsil ODS3 column (GL Sciences); 3 µm; 4.6 mm×150 mm] at a flow rate of 1.0 ml min$^{-1}$. After injection on to a column equilibrated with the mobile phase, methanol/isopropanol (3:1, v/v), the column was eluted by an isocratic mobile phase for 30 min. The molecular mass of ubiquinone eluted from 8.5 min of A in FIG. 8 and 10.2 min of B in FIG. 8 were measured by LC-MS and shown in A and B in FIG. 9, respectively. These charts demonstrate that the peak at 8.5 min is ubiquinone-9 [m/z 818 (M+Na)$^+$] and that the peak at 10.2 min is ubiquinone-10 [m/z 886 (M+Na)$^+$].

Figure 10:
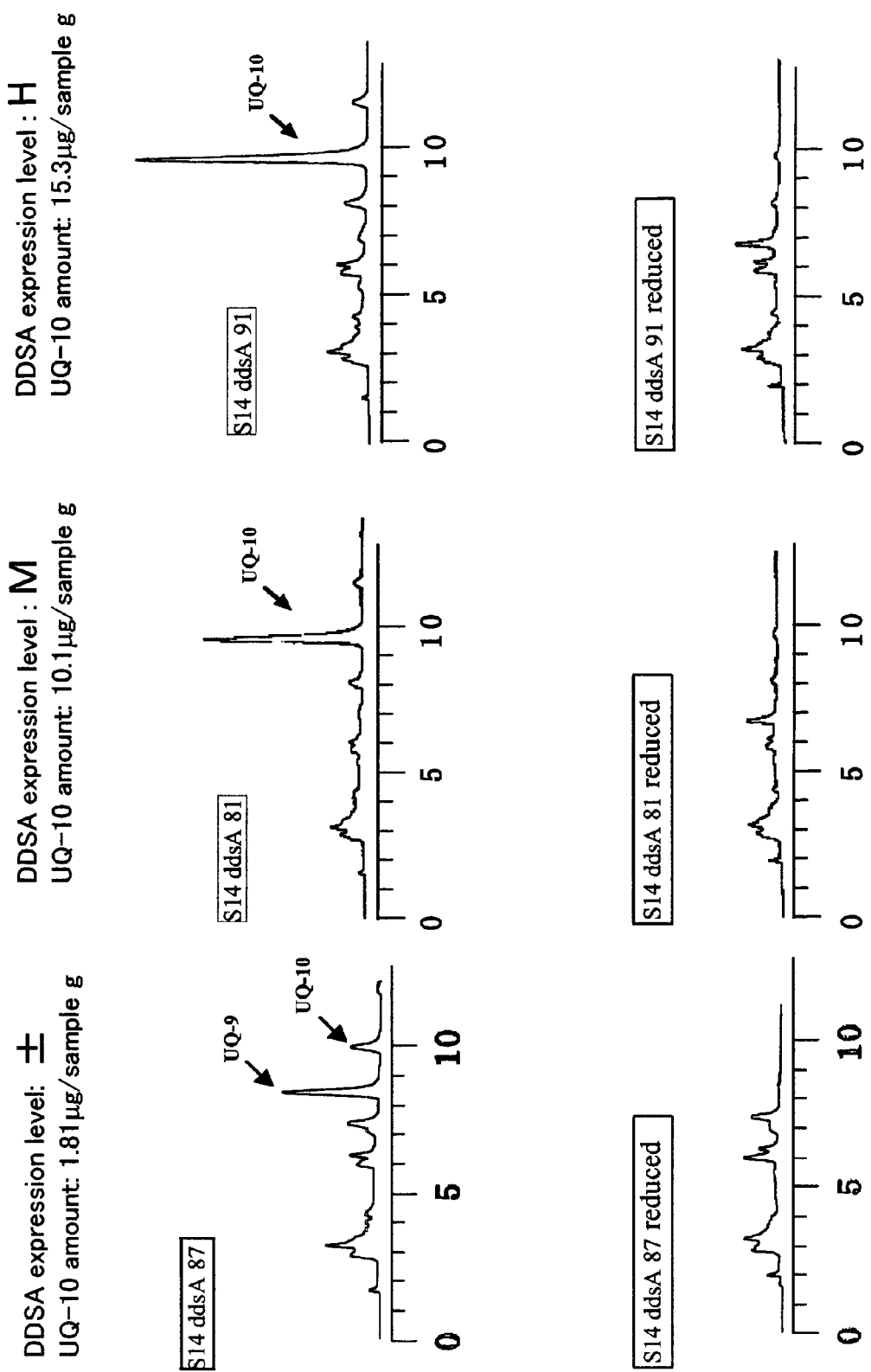
FIG. 10 shows a comparison of amounts of produced ubiquinone in transgenic plants in which S14-DDSA is expressed at various expression levels.

Transgenic plant expressing ddsA produced ubiquinone-10 (FIG. 10). When ubiquinone (oxidized type) is reduced, the ubiquinone is converted to ubiquinol (reduced type), resulting in disappearance of absorption of 275-nm ultraviolet. Therefore, an absorption peak at which 275-nm ultraviolet disappears indicates the presence of ubiquinone.

Example 6

Extraction and Measurement of Ubiquinone-10 from Brown Rice

Progeny of the rice produced in Example 2 was prepared. Brown rice was obtained from the progeny.

The brown rice was used to extract and measure ubiquinone in accordance with the method of Example 5. The result is shown in FIG. 11.

Figure 11:
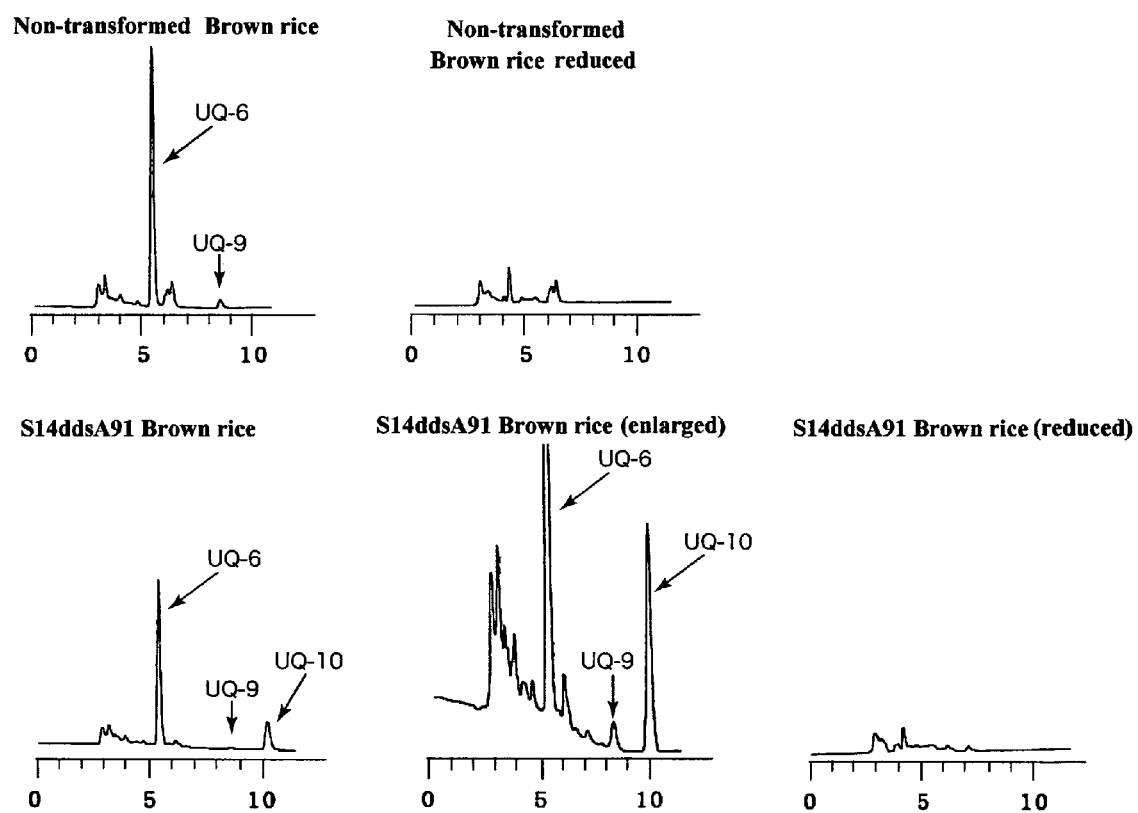
FIG. 11 shows that extremely low amount of ubiquinone-10 is detected in non-transformed brown rice (upper left), while ubiquinone-10 is detected in brown rice which expresses S14-DDSA (lower left, lower middle (enlarged view)), indicating production of ubiquinone-10.

FIG. 11 shows the amounts of produced ubiquinone-9 and ubiquinone-10 in brown rice of non-transformed plants, and transgenic plants in which S14-DDSA was expressed. Note that ubiquinone-6 was added as an internal reference for measurement.

As can be seen from the result, whereas ubiquinone-10 production was not confirmed in the brown rice of non-transformed plant, a larger amount of ubiquinone-10 than that of ubiquinone-9 was accumulated in brown rice of a plant which expressed S14-DDSA.

According to Example 6, it was demonstrated that the present invention provides brown rice which is a satisfactory source for ubiquinone-10.

Although certain preferred embodiments have been described herein, it is not intended that such embodiments be construed as limitations on the scope of the invention except as set forth in the appended claims. Various other modifications and equivalents will be apparent to and can be readily made by those skilled in the art, after reading the description herein, without departing from the scope and spirit of this invention. All patents, published patent applications and publications cited herein are incorporated by reference as if set forth fully herein.

What is claimed is:

1. A plant which is transformed using an expression cassette which expresses decaprenyl diphosphate synthase, encoded by:
   a nucleic acid encoding a polypeptide having an amino acid sequence as set forth in SEQ ID NO:6,
   wherein said plant is a Gramineae plant which produces ubiquinone-9,
   wherein the decaprenyl diphosphate synthase maintains a physiological activity of producing ubiquinone-10 at a level greater than the level of ubiquinone-9 produced; and
   wherein an amount of ubiquinone-10 larger than that of ubiquinone-9 is accumulated in the plant.

2. A plant according to claim 1, wherein a nucleic acid encoding the decaprenyl diphosphate synthase is operatively linked with a nucleic acid encoding a mitochondrial targeting sequence.

3. A plant according to claim 2, wherein the nucleic acid encoding the mitochondrial targeting sequence is selected from the group consisting of a nucleic acid encoding a fragment of rice RPS10 protein (SEQ ID NO. 2), a nucleic acid encoding a fragment of RPS14 protein (SEQ ID NO. 4), a nucleic acid encoding a fragment of RPS11 protein, a nucleic acid encoding a fragment of ATPase β-subunit protein (SEQ ID NO. 10), and a nucleic acid encoding a fragment of ATPase g-subunit protein (SEQ ID NO. 12).

4. A plant according to claim 2, wherein the mitochondrial targeting sequence is a fragment consisting of amino acids 1 to 56 of rice RPS10 protein (SEQ ID NO. 2).

5. A plant according to claim 2, wherein the mitochondrial targeting sequence is a fragment consisting of an amino acid sequence of amino acids 1 to 48 of rice RPS14 protein (SEQ ID NO. 4).

6. A plant according to claim 1, wherein the decaprenyl diphosphate synthase gene is operatively linked with a seed-specific promoter.

7. A plant according to claim 1, wherein the plant is selected from the group consisting of a plant cell, a plant culture cell, a plant seed, a regenerated plant, a plant callus, plant tissue, a leaf, a stem, a root, a flower, and a seeding.

8. A seed from a plant according to any one of claims 1, 2, 3, 4, 5, or 6, wherein the seed comprises exogenous decaprenyl diphosphate synthase.

9. A plant which contains an expression cassette which expresses decaprenyl diphosphate synthase encoded by a nucleic acid encoding a polypeptide having an amino acid sequence set forth in SEQ ID NO:6,
   wherein said plant is a Gramineae plant which produces ubiquinone-9, and
   wherein the decaprenyl diphosphate synthase maintains physiological activity of producing ubiquinone-10 at a level greater than the level of ubiquinone-9 produced, wherein an amount of ubiquinone-10 larger than that of ubiquinone-9 is accumulated in the plant.

10. A seed of a plant according to claim 9, wherein the seed comprises exogenous decaprenyl diphosphate synthase.

11. A method for producing ubiquinone-10 using a plant, comprising: preparing a plant according to claim 1; and culturing the plant.

12. Plant tissue which is obtained from a plant according to claim 1 and contains ubiquinone-10.

13. A plant cell which is obtained from a plant according to claim 1 and contains ubiquinone-10.

14. A plant according to claim 1, wherein the decaprenyl diphosphate synthase is encoded by the sequence complementary to SEQ ID NO. 5.

* * * * *

SEQUENCE LISTING

```
<160> NUMBER OF SEQ ID NOS: 12

<210> SEQ ID NO 1
<211> LENGTH: 2500
<212> TYPE: DNA
<213> ORGANISM: Oryza sativa
<220> FEATURE:
<221> NAME/KEY: CDS
<222> LOCATION: (1641)..(1979)
<223> OTHER INFORMATION:

<400> SEQUENCE: 1
gagccacgtc aatttgatgg taaattcgct gcttcatcaa actttgcagg tacacgtgct      60
gccagttgct gggctttcat gggctgtgat gggctggttt ccgtgggctg ttgagtgggt     120
gtgcgcacga gccgttggat cggcttggac gatggatatt acacttgact gcacgctggt     180
atctgaggat cctactcccc cagtccccg cgagcgagca gaggcggcgc cgtcgctcgt      240
cctccgccac cgccgccggc gccgataccc atccatcccg cgccgcgagc gagtgcttcc     300
gccgcatcca tcctggttag cacaccctct ttcccatctc tctctctcta ctcacgcacc     360
taccgaattc gcgttaaccc tagcttctgt tctagaaatt ttgccttaac cttagtacta     420
atttcttccc aaaaagtttt ggggtgtccc atgttagatc cgtccatgaa ttaagctgcc     480
tgtcgaaccg gttattctct ggtataactc ctgtcaatgt actctgcctc agttcttgat     540
tgggaaacct ttccttgcta gttgctacct aattttcagt ttttcatcat tgtacttcag     600
cttgtgactt actggattaa tcagttggga tggagtatat gttggatgaa ctcgtataaa     660
ttggtagtat gcaaattttg gagactcata attgtgagag ttatctagct ttatttgttg     720
ccgttcactt gtttctctag tcaaagatgc ttgtcttgaa gttgatgatg ttagcctttt     780
taagattcaa tcaatgatgc taaagtattt attcaatata ctaattgcaa ttagggttgt     840
tcgcccattt acaactggtg taaacgagct tagcttagct gtcgcgtgct tgctgaaaat     900
gaatacagcc agttgttcgg tcaaaacctc cgatgaacag cccttattgc aacatagttg     960
tatctgtcat aagattatct tctctatttt tgttatgccg tgggcttatt gactgaggtt    1020
gtaatcgtgc aaaacaggag gacagggtac tgggtgtggg caggcaggca ctgaaactgg    1080
actacactct agcttcttag tgattacctc tagatcagct cagcaaatag atgctattaa    1140
ccactttgtt tacaacttta catgcatgat aatcgttttt gtatcctgaa catgagaatt    1200
tgaaatttgt agtaggtgtc aattacttca ccaagtaaag tagctggaaa catatactag    1260
tagccatgcg ggagtctggt cttccaaatc aatcaaacaa tctgtgactg ggtatcatat    1320
tgcacattaa tatgtatgct aaaggtccta tgtttaaact gttactagaa gtgcttatat    1380
ttgtttgcct tcctgctgct cttgtactat attctagatt caaatgtaca acatcttatt    1440
gctcatgtaa acattaaata ctaattgtaa ctgtctaaat ttcttcagag tttttagtgc    1500
ttactaaatt tcttcagatt ttccgtttgc tgtctaaaac tcttaaaagc atcatgtttt    1560
catgagaaag ctaacgttta cagtctcctg gtgtgaaggg catttgcaat cagtgacaaa    1620
agttcctcag ctgtggagcc atg gcc gcc aag ata cgc ata gtg atg aaa tct    1673
                       Met Ala Ala Lys Ile Arg Ile Val Met Lys Ser
                         1               5                  10
```

```
ttt atg agc caa gct aac aaa gtt gaa ggg gtt att cca tac gcg cag        1721
Phe Met Ser Gln Ala Asn Lys Val Glu Gly Val Ile Pro Tyr Ala Gln
            15                  20                  25 aag gtt gga ttg cct gaa tca cga tcc ttg tat acc gtg cta cga tcg        1769
Lys Val Gly Leu Pro Glu Ser Arg Ser Leu Tyr Thr Val Leu Arg Ser
        30                  35                  40 cct cac ata gac aag aag tcg agg gag cag ttc tcg atg cat gtc aag        1817
Pro His Ile Asp Lys Lys Ser Arg Glu Gln Phe Ser Met His Val Lys
    45                  50                  55 aaa caa ttt ctg gta cag aag gcg gag acg cac gag ctg cag aag aag        1865
Lys Gln Phe Leu Val Gln Lys Ala Glu Thr His Glu Leu Gln Lys Lys
60                  65                  70                  75 ctg ttc tgg ttg aag cgc ctg cgc ctg ctt ggt gct cag tat gaa ctc        1913
Leu Phe Trp Leu Lys Arg Leu Arg Leu Leu Gly Ala Gln Tyr Glu Leu
                80                  85                  90 cag atc agt ttc aag acc cgt ttg gac aag aag ctg ctc caa gct gct        1961
Gln Ile Ser Phe Lys Thr Arg Leu Asp Lys Lys Leu Leu Gln Ala Ala
            95                  100                 105 ttg tcg tca ggt tgc tag agcacttcac ttaccaccat tcacccttga              2009
Leu Ser Ser Gly Cys
            110 acaagactgc ttttgcttct atgatgtctt catgatgaga ttgtcaaaca gtacttgcat      2069 ccattaagca tttcatatga tgaaactaca ccatttggaa gagtttgaag gaatgtagta      2129 gtaatccatc caaaacgttc agatgctctg aattatgaag atgtggcatg atatgaaaca     2189 gatatccttc cgtttccggg cttctctttg gttttgttcc gaatgccgtt taacaagtca     2249 tgacattcct atactttgct ccctgtgtta agatgtttta gggttgtctg taagtcaaac     2309 tttttcaagt ttgcttaaat ttatagaaaa aagatttta cacaaaataa ttataccagg      2369 aaaatatatt ccatggtaga tctaatgtaa ccaatttggt gttatagatg ttactacatt     2429 tttctataaa tttgattaaa tttaaagaag tttgatttag agcaaaacct aaatatcttg     2489 caaagtatct t                                                          2500

<210> SEQ ID NO 2
<211> LENGTH: 112
<212> TYPE: PRT
<213> ORGANISM: Oryza sativa

<400> SEQUENCE: 2

Met Ala Ala Lys Ile Arg Ile Val Met Lys Ser Phe Met Ser Gln Ala
1               5                   10                  15

Asn Lys Val Glu Gly Val Ile Pro Tyr Ala Gln Lys Val Gly Leu Pro
            20                  25                  30

Glu Ser Arg Ser Leu Tyr Thr Val Leu Arg Ser Pro His Ile Asp Lys
        35                  40                  45

Lys Ser Arg Glu Gln Phe Ser Met His Val Lys Gln Phe Leu Val
    50                  55                  60

Gln Lys Ala Glu Thr His Glu Leu Gln Lys Lys Leu Phe Trp Leu Lys
65                  70                  75                  80

Arg Leu Arg Leu Leu Gly Ala Gln Tyr Glu Leu Gln Ile Ser Phe Lys
                85                  90                  95

Thr Arg Leu Asp Lys Lys Leu Leu Gln Ala Ala Leu Ser Ser Gly Cys
            100                 105                 110

<210> SEQ ID NO 3
<211> LENGTH: 1233
```

```
<212> TYPE: DNA
<213> ORGANISM: Oryza sativa
<220> FEATURE:
<221> NAME/KEY: CDS
<222> LOCATION: (21)..(1073)
<223> OTHER INFORMATION:

<400> SEQUENCE: 3
gaaaccccaa atccgccgcg atg gcc gcc gcc gcc ctc ctc cgc cgc tcg ccg    53
                     Met Ala Ala Ala Ala Leu Leu Arg Arg Ser Pro
                      1               5                  10 gcg gcg cgc gcc ctc ctc tcc ccg gcg ctc tcc tcc cgc ctc gtc gcc     101
Ala Ala Arg Ala Leu Leu Ser Pro Ala Leu Ser Ser Arg Leu Val Ala
            15                  20                  25 tcc aag ccc cac tcg tcg tcc ccc gcg ccg ccg ccg ccg tcg aag         149
Ser Lys Pro His Ser Ser Ser Pro Ala Pro Pro Pro Pro Ser Lys
        30                  35                  40 gcg ggg gcg aac acc aag acg ttc tcg atc tac agg tgg gat ccc gac     197
Ala Gly Ala Asn Thr Lys Thr Phe Ser Ile Tyr Arg Trp Asp Pro Asp
45                  50                  55 tcg ccg tcg acg aag ccc cac ctc aag gac tac aag gtg gac ctc tcc     245
Ser Pro Ser Thr Lys Pro His Leu Lys Asp Tyr Lys Val Asp Leu Ser
60                  65                  70                  75 gac tgc ggg ccg atg gtg ctc gac gtg ctg ctc aag atc aag aac gag     293
Asp Cys Gly Pro Met Val Leu Asp Val Leu Leu Lys Ile Lys Asn Glu
                80                  85                  90 cag gac ccg tcg ctc acc ttc cgc cgc agc tgc cgc gag ggg atc tgc     341
Gln Asp Pro Ser Leu Thr Phe Arg Arg Ser Cys Arg Glu Gly Ile Cys
            95                  100                 105 ggg agc tgc gcg atg aac atc gac ggc gac aat ggc ctc gcc tgc ctc     389
Gly Ser Cys Ala Met Asn Ile Asp Gly Asp Asn Gly Leu Ala Cys Leu
        110                 115                 120 acc aag atc tcg tcg gcg tcc tcg gcc tcc acg atc tcg ccg ctc ccc     437
Thr Lys Ile Ser Ser Ala Ser Ser Ala Ser Thr Ile Ser Pro Leu Pro
125                 130                 135 cac atg ttc gtc atc aag gac ctc gtc gtc gac atg acc aac ttc tac     485
His Met Phe Val Ile Lys Asp Leu Val Val Asp Met Thr Asn Phe Tyr
140                 145                 150                 155 aac cag tac aag agc gtg gag ccg tgg ctc aag cgc aag gac gcg ccg     533
Asn Gln Tyr Lys Ser Val Glu Pro Trp Leu Lys Arg Lys Asp Ala Pro
                160                 165                 170 ccg cag ccc ggg aag gag atc ccg cag acc aag gcc gac cgc gcc aag     581
Pro Gln Pro Gly Lys Glu Ile Pro Gln Thr Lys Ala Asp Arg Ala Lys
            175                 180                 185 ctc gac ggc atg tac gag tgc atc ctc tgc gcc tgc tgc tcc acc tcc     629
Leu Asp Gly Met Tyr Glu Cys Ile Leu Cys Ala Cys Cys Ser Thr Ser
        190                 195                 200 tgc ccc tcc tac tgg tgg aac ccc gag gag tac ctc ggc ccc gcc gcg     677
Cys Pro Ser Tyr Trp Trp Asn Pro Glu Glu Tyr Leu Gly Pro Ala Ala
205                 210                 215 ctc ctc cac gcc aac agg ctt ccg ctg ttg ggg acg cta atc aaa cca     725
Leu Leu His Ala Asn Arg Leu Pro Leu Leu Gly Thr Leu Ile Lys Pro
220                 225                 230                 235 aaa ccc aac atg ttc atg cac atc caa gct cga gga tat cac ggg gta    773
Lys Pro Asn Met Phe Met His Ile Gln Ala Arg Gly Tyr His Gly Val
                240                 245                 250 tcg gag aag aga aac ttg ctg gat cac aaa cgt aga ttg ctt gca gca    821
Ser Glu Lys Arg Asn Leu Leu Asp His Lys Arg Arg Leu Leu Ala Ala
            255                 260                 265 aaa tat gaa ctg aaa gga aag ctt tat aag gct gtt tgt agg gac cct    869
Lys Tyr Glu Leu Lys Gly Lys Leu Tyr Lys Ala Val Cys Arg Asp Pro
```

```
                   270                 275                 280
gat ctt cca gca gat atg cag gac cag ttt cgc tat aag ctg tcc aag       917
Asp Leu Pro Ala Asp Met Gln Asp Gln Phe Arg Tyr Lys Leu Ser Lys
    285                 290                 295 ttg cca aga aat agc tcc atg aca cgc ctt aga aac cgc tgt atc ttc       965
Leu Pro Arg Asn Ser Ser Met Thr Arg Leu Arg Asn Arg Cys Ile Phe
300                 305                 310                 315 acg ggc cgc tcg cgc gct gtt tac aag aaa ttc cgc atg tct cgt att      1013
Thr Gly Arg Ser Arg Ala Val Tyr Lys Lys Phe Arg Met Ser Arg Ile
                320                 325                 330 gtg ttc cgg tca ttg gct aat aag ggt gaa ttg ttg ggt gtt aag aaa      1061
Val Phe Arg Ser Leu Ala Asn Lys Gly Glu Leu Leu Gly Val Lys Lys
                335                 340                 345 gcg tct tgg tag atgctaacaa ccagtagatc aaagcactag ctctgcagta          1113
Ala Ser Trp
        350 gtccagcaca ataagtttgc ctccatgcag tttttcagtg tttgcaacct gaaactatat    1173 ttcaatctta tgaccagcag ccaatctggc actctttcaa ttaaaaaaaa aaaaaaaaaa    1233

<210> SEQ ID NO 4
<211> LENGTH: 350
<212> TYPE: PRT
<213> ORGANISM: Oryza sativa

<400> SEQUENCE: 4

Met Ala Ala Ala Leu Leu Arg Arg Ser Pro Ala Ala Arg Ala Leu
1               5                   10                  15

Leu Ser Pro Ala Leu Ser Ser Arg Leu Val Ala Ser Lys Pro His Ser
                20                  25                  30

Ser Ser Pro Ala Pro Pro Pro Ser Lys Ala Gly Ala Asn Thr
            35                  40                  45

Lys Thr Phe Ser Ile Tyr Arg Trp Asp Pro Asp Ser Pro Ser Thr Lys
    50                  55                  60

Pro His Leu Lys Asp Tyr Lys Val Asp Leu Ser Asp Cys Gly Pro Met
65                  70                  75                  80

Val Leu Asp Val Leu Leu Lys Ile Lys Asn Glu Gln Asp Pro Ser Leu
                85                  90                  95

Thr Phe Arg Arg Ser Cys Arg Glu Gly Ile Cys Gly Ser Cys Ala Met
                100                 105                 110

Asn Ile Asp Gly Asp Asn Gly Leu Ala Cys Leu Thr Lys Ile Ser Ser
            115                 120                 125

Ala Ser Ser Ala Ser Thr Ile Ser Pro Leu Pro His Met Phe Val Ile
    130                 135                 140

Lys Asp Leu Val Val Asp Met Thr Asn Phe Tyr Asn Gln Tyr Lys Ser
145                 150                 155                 160

Val Glu Pro Trp Leu Lys Arg Lys Asp Ala Pro Pro Gln Pro Gly Lys
                165                 170                 175

Glu Ile Pro Gln Thr Lys Ala Asp Arg Ala Lys Leu Asp Gly Met Tyr
            180                 185                 190

Glu Cys Ile Leu Cys Ala Cys Cys Ser Thr Ser Cys Pro Ser Tyr Trp
    195                 200                 205

Trp Asn Pro Glu Glu Tyr Leu Gly Pro Ala Ala Leu Leu His Ala Asn
                210                 215                 220

Arg Leu Pro Leu Leu Gly Thr Leu Ile Lys Pro Lys Pro Asn Met Phe
225                 230                 235                 240
```

```
Met His Ile Gln Ala Arg Gly Tyr His Gly Val Ser Glu Lys Arg Asn
                245                 250                 255

Leu Leu Asp His Lys Arg Arg Leu Leu Ala Ala Lys Tyr Glu Leu Lys
            260                 265                 270

Gly Lys Leu Tyr Lys Ala Val Cys Arg Asp Pro Asp Leu Pro Ala Asp
        275                 280                 285

Met Gln Asp Gln Phe Arg Tyr Lys Leu Ser Lys Leu Pro Arg Asn Ser
    290                 295                 300

Ser Met Thr Arg Leu Arg Asn Arg Cys Ile Phe Thr Gly Arg Ser Arg
305                 310                 315                 320

Ala Val Tyr Lys Lys Phe Arg Met Ser Arg Ile Val Phe Arg Ser Leu
                325                 330                 335

Ala Asn Lys Gly Glu Leu Leu Gly Val Lys Lys Ala Ser Trp
            340                 345                 350

<210> SEQ ID NO 5
<211> LENGTH: 948
<212> TYPE: DNA
<213> ORGANISM: Gluconobacter suboxydans
<220> FEATURE:
<221> NAME/KEY: CDS
<222> LOCATION: (1)..(948)
<223> OTHER INFORMATION:

<400> SEQUENCE: 5 atg ctg gcc tgc aac cgg gcg atc atc gcc cgg atg gaa agt ccg gtt     48
Met Leu Ala Cys Asn Arg Ala Ile Ile Ala Arg Met Glu Ser Pro Val
1               5                   10                  15 ccc ctg atc ccg cag ctt ggc gcc cat ctt gtc gcg gcg gga ggc aag     96
Pro Leu Ile Pro Gln Leu Gly Ala His Leu Val Ala Ala Gly Gly Lys
                20                  25                  30 cgc ctt cgc ccg ctg ctg acg ctg gcc tcc gca cgt ctg tgc ggt tat    144
Arg Leu Arg Pro Leu Leu Thr Leu Ala Ser Ala Arg Leu Cys Gly Tyr
            35                  40                  45 cag ccg ggt ccg gac cat cag cgt cat gtc ggg ctc gcc gcc tgc gtt    192
Gln Pro Gly Pro Asp His Gln Arg His Val Gly Leu Ala Ala Cys Val
        50                  55                  60 gag ttc att cat acc gcc aca ctg ctg cat gat gat gtc gtg gat gag    240
Glu Phe Ile His Thr Ala Thr Leu Leu His Asp Asp Val Val Asp Glu
65                  70                  75                  80 agc acg ttg cgt cgg ggg ctg gct tcg gcc aat gcc gtg ttc ggc aac    288
Ser Thr Leu Arg Arg Gly Leu Ala Ser Ala Asn Ala Val Phe Gly Asn
                85                  90                  95 aag gcg tcc gtg ctg gta ggt gac ttc ctg ttc gcc cgc tcg ttc cag    336
Lys Ala Ser Val Leu Val Gly Asp Phe Leu Phe Ala Arg Ser Phe Gln
                100                 105                 110 ctt atg aca gca gac ggc tcc ctg aag gtc atg gcg atc ctg tcg gat    384
Leu Met Thr Ala Asp Gly Ser Leu Lys Val Met Ala Ile Leu Ser Asp
            115                 120                 125 gca tcg gcg aca att gct gaa ggt gaa gtc ctt cag atg gtc gtg cag    432
Ala Ser Ala Thr Ile Ala Glu Gly Glu Val Leu Gln Met Val Val Gln
        130                 135                 140 aac gac ctt acg acg cct gta gaa cgc tat ctt gaa gtc att cac ggc    480
Asn Asp Leu Thr Thr Pro Val Glu Arg Tyr Leu Glu Val Ile His Gly
145                 150                 155                 160 aag acg gct gcg ctg ttt gcg gct gcc tgc cgt gtc ggc gct gtc gtg    528
Lys Thr Ala Ala Leu Phe Ala Ala Ala Cys Arg Val Gly Ala Val Val
                165                 170                 175 gcc gag cgt ccg gaa gca gaa gag gaa gct ctg gag cgg ttt ggc acc    576
Ala Glu Arg Pro Glu Ala Glu Glu Glu Ala Leu Glu Arg Phe Gly Thr
```

```
                180                 185                 190
aat ctg ggt atg gcg ttc cag ctt gtt gat gat gcc ctg gat tat gcc    624
Asn Leu Gly Met Ala Phe Gln Leu Val Asp Asp Ala Leu Asp Tyr Ala
        195                 200                 205 gca gac cag cag gtt ttg ggc aag acc gtt ggt gat gac atg cgt gaa    672
Ala Asp Gln Gln Val Leu Gly Lys Thr Val Gly Asp Asp Met Arg Glu
210                 215                 220 ggc aag atc acc ctg ccg gtc ctg gcc gcc tat gag gct ggc tcg ccg    720
Gly Lys Ile Thr Leu Pro Val Leu Ala Ala Tyr Glu Ala Gly Ser Pro
225                 230                 235                 240 gaa gat cgt att ttc tgg gag cgc gtc att gga gaa ggg gag cag act    768
Glu Asp Arg Ile Phe Trp Glu Arg Val Ile Gly Glu Gly Glu Gln Thr
            245                 250                 255 gag gac gat ctg cct cat gct ctg aac ctg att gca aag acg ggt gcg    816
Glu Asp Asp Leu Pro His Ala Leu Asn Leu Ile Ala Lys Thr Gly Ala
        260                 265                 270 atc aat acg acg atc gcc cgc gcg cag gtc tat gcc gac gca gct gtt    864
Ile Asn Thr Thr Ile Ala Arg Ala Gln Val Tyr Ala Asp Ala Ala Val
    275                 280                 285 gaa gcc ctg tcc att ttc ccg gat agc gaa ctg cgc cgc ctt ctg atc    912
Glu Ala Leu Ser Ile Phe Pro Asp Ser Glu Leu Arg Arg Leu Leu Ile
290                 295                 300 gaa acg gtt cag ttc acg gtg aat cgg gcc cgc taa                    948
Glu Thr Val Gln Phe Thr Val Asn Arg Ala Arg
305                 310                 315

<210> SEQ ID NO 6
<211> LENGTH: 315
<212> TYPE: PRT
<213> ORGANISM: Gluconobacter suboxydans

<400> SEQUENCE: 6

Met Leu Ala Cys Asn Arg Ala Ile Ile Ala Arg Met Glu Ser Pro Val
1               5                   10                  15

Pro Leu Ile Pro Gln Leu Gly Ala His Leu Val Ala Ala Gly Gly Lys
            20                  25                  30

Arg Leu Arg Pro Leu Leu Thr Leu Ala Ser Ala Arg Leu Cys Gly Tyr
        35                  40                  45

Gln Pro Gly Pro Asp His Gln Arg His Val Gly Leu Ala Ala Cys Val
    50                  55                  60

Glu Phe Ile His Thr Ala Thr Leu Leu His Asp Asp Val Val Asp Glu
65                  70                  75                  80

Ser Thr Leu Arg Arg Gly Leu Ala Ser Ala Asn Ala Val Phe Gly Asn
                85                  90                  95

Lys Ala Ser Val Leu Val Gly Asp Phe Leu Phe Ala Arg Ser Phe Gln
            100                 105                 110

Leu Met Thr Ala Asp Gly Ser Leu Lys Val Met Ala Ile Leu Ser Asp
        115                 120                 125

Ala Ser Ala Thr Ile Ala Glu Gly Glu Val Leu Gln Met Val Val Gln
    130                 135                 140

Asn Asp Leu Thr Thr Pro Val Glu Arg Tyr Leu Glu Val Ile His Gly
145                 150                 155                 160

Lys Thr Ala Ala Leu Phe Ala Ala Ala Cys Arg Val Gly Ala Val Val
                165                 170                 175

Ala Glu Arg Pro Glu Ala Glu Glu Ala Leu Glu Arg Phe Gly Thr
            180                 185                 190

Asn Leu Gly Met Ala Phe Gln Leu Val Asp Asp Ala Leu Asp Tyr Ala
```

```
                195                 200                 205
Ala Asp Gln Gln Val Leu Gly Lys Thr Val Gly Asp Met Arg Glu
    210                 215                 220
Gly Lys Ile Thr Leu Pro Val Leu Ala Ala Tyr Glu Ala Gly Ser Pro
225                 230                 235                 240
Glu Asp Arg Ile Phe Trp Glu Arg Val Ile Gly Glu Gly Gln Thr
                245                 250                 255
Glu Asp Asp Leu Pro His Ala Leu Asn Leu Ile Ala Lys Thr Gly Ala
            260                 265                 270
Ile Asn Thr Thr Ile Ala Arg Ala Gln Val Tyr Ala Asp Ala Ala Val
            275                 280                 285
Glu Ala Leu Ser Ile Phe Pro Asp Ser Glu Leu Arg Arg Leu Leu Ile
        290                 295                 300
Glu Thr Val Gln Phe Thr Val Asn Arg Ala Arg
305                 310                 315

<210> SEQ ID NO 7
<211> LENGTH: 2031
<212> TYPE: DNA
<213> ORGANISM: Nicotiana tabacum
<220> FEATURE:
<221> NAME/KEY: CDS
<222> LOCATION: (77)..(1417)
<223> OTHER INFORMATION:

<400> SEQUENCE: 7
ccacggatga aacactcata actgaacagt gatagactat tcgctttctc ctaaagcctt      60
caatcgaaat cgcacg atg aga ggg tac aag ttt tgc tgt gat ttc cgg tac     112
               Met Arg Gly Tyr Lys Phe Cys Cys Asp Phe Arg Tyr
                 1               5                  10 ctc ctc atc ttg gct gct gtc gcc ttc atc tac ata cag atg cgg ctt       160
Leu Leu Ile Leu Ala Ala Val Ala Phe Ile Tyr Ile Gln Met Arg Leu
         15                  20                  25 ttt gcg aca cag tca gaa tat gca gat cgc ctt gct gct gca att gaa       208
Phe Ala Thr Gln Ser Glu Tyr Ala Asp Arg Leu Ala Ala Ala Ile Glu
     30                  35                  40 gca gaa aat cac tgt aca agt cag acc aga ttg ctt att gac cag att       256
Ala Glu Asn His Cys Thr Ser Gln Thr Arg Leu Leu Ile Asp Gln Ile
45                  50                  55                  60 agc cag cag caa gga aga ata gtt gct ctt gaa gaa caa atg aag cgt       304
Ser Gln Gln Gln Gly Arg Ile Val Ala Leu Glu Glu Gln Met Lys Arg
                 65                  70                  75 cag gac cag gag tgc cga cag tta agg gct ctt gtt cag gat ctt gaa       352
Gln Asp Gln Glu Cys Arg Gln Leu Arg Ala Leu Val Gln Asp Leu Glu
             80                  85                  90 agt aag ggc ata aaa aag ttg atc gga aat gta cag atg cca gtg gct       400
Ser Lys Gly Ile Lys Lys Leu Ile Gly Asn Val Gln Met Pro Val Ala
         95                 100                 105 gct gta gtt gtt atg gct tgc aat cgg gct gac tac ctg gaa aag act       448
Ala Val Val Val Met Ala Cys Asn Arg Ala Asp Tyr Leu Glu Lys Thr
     110                 115                 120 att aaa tcc atc tta aaa tac caa ata tct gtt gcg cca aaa tat cct       496
Ile Lys Ser Ile Leu Lys Tyr Gln Ile Ser Val Ala Pro Lys Tyr Pro
125                 130                 135                 140 ctt ttc ata tcc cag gat gga tca cat cct gat gtt agg aag ctt gct       544
Leu Phe Ile Ser Gln Asp Gly Ser His Pro Asp Val Arg Lys Leu Ala
                145                 150                 155 ttg agc tat gat cag ctg acg tat atg cag cac ttg gat ttt gaa cct       592
Leu Ser Tyr Asp Gln Leu Thr Tyr Met Gln His Leu Asp Phe Glu Pro
```

-continued

|  |  | 160 |  |  |  | 165 |  |  |  | 170 |  |  |  |
|---|---|---|---|---|---|---|---|---|---|---|---|---|---|
| gtg | cat | act | gaa | aga | cca | ggg | gag | ctg | att | gca | tac | tac | aaa att gca | 640 |
| Val | His | Thr | Glu | Arg | Pro | Gly | Glu | Leu | Ile | Ala | Tyr | Tyr | Lys Ile Ala |
|  |  | 175 |  |  |  | 180 |  |  |  | 185 |  |  |  |

| cgt | cat | tac | aag | tgg | gca | ttg | gat | cag | ctg | ttt | tac | aag | cat aat ttt | 688 |
| Arg | His | Tyr | Lys | Trp | Ala | Leu | Asp | Gln | Leu | Phe | Tyr | Lys | His Asn Phe |
|  | 190 |  |  |  |  | 195 |  |  |  |  | 200 |  |  |

| agc | cgt | gtt | atc | ata | cta | gaa | gat | gat | atg | gaa | att | gcc | cct gat ttt | 736 |
| Ser | Arg | Val | Ile | Ile | Leu | Glu | Asp | Asp | Met | Glu | Ile | Ala | Pro Asp Phe |
| 205 |  |  |  |  | 210 |  |  |  |  | 215 |  |  | 220 |

| ttt | gac | ttt | ttt | gag | gct | gga | gct | act | ctt | ctt | gac | aga | gac aag tcg | 784 |
| Phe | Asp | Phe | Phe | Glu | Ala | Gly | Ala | Thr | Leu | Leu | Asp | Arg | Asp Lys Ser |
|  |  |  |  | 225 |  |  |  |  | 230 |  |  |  | 235 |

| att | atg | gct | att | tct | tct | tgg | aat | gac | aat | gga | caa | atg | cag ttt gtc | 832 |
| Ile | Met | Ala | Ile | Ser | Ser | Trp | Asn | Asp | Asn | Gly | Gln | Met | Gln Phe Val |
|  |  |  | 240 |  |  |  |  | 245 |  |  |  |  | 250 |

| caa | gat | cct | tat | gct | ctt | tac | cgc | tct | gat | ttt | ttt | ccc | ggt ctt gga | 880 |
| Gln | Asp | Pro | Tyr | Ala | Leu | Tyr | Arg | Ser | Asp | Phe | Phe | Pro | Gly Leu Gly |
|  |  | 255 |  |  |  |  | 260 |  |  |  |  | 265 |  |

| tgg | atg | ctt | tca | aaa | tct | act | tgg | gac | gaa | cta | tct | cca | aag tgg cca | 928 |
| Trp | Met | Leu | Ser | Lys | Ser | Thr | Trp | Asp | Glu | Leu | Ser | Pro | Lys Trp Pro |
|  | 270 |  |  |  |  | 275 |  |  |  |  | 280 |  |  |

| aag | gct | tac | tgg | gac | gac | tgg | cta | aga | ctc | aaa | gag | aat | cac aga ggt | 976 |
| Lys | Ala | Tyr | Trp | Asp | Asp | Trp | Leu | Arg | Leu | Lys | Glu | Asn | His Arg Gly |
| 285 |  |  |  |  | 290 |  |  |  |  | 295 |  |  | 300 |

| cga | caa | ttt | att | cgc | cca | gaa | gtt | tgc | aga | tca | tat | aat | ttt ggt gag | 1024 |
| Arg | Gln | Phe | Ile | Arg | Pro | Glu | Val | Cys | Arg | Ser | Tyr | Asn | Phe Gly Glu |
|  |  |  |  | 305 |  |  |  |  | 310 |  |  |  | 315 |

| cat | ggt | tct | agt | ttg | ggg | cag | ttt | ttc | aag | cag | tat | ctt | gag cca att | 1072 |
| His | Gly | Ser | Ser | Leu | Gly | Gln | Phe | Phe | Lys | Gln | Tyr | Leu | Glu Pro Ile |
|  |  |  | 320 |  |  |  |  | 325 |  |  |  |  | 330 |

| aaa | cta | aat | gat | gtc | cag | gtt | gat | tgg | aag | tca | atg | gac | ctt agt tac | 1120 |
| Lys | Leu | Asn | Asp | Val | Gln | Val | Asp | Trp | Lys | Ser | Met | Asp | Leu Ser Tyr |
|  |  | 335 |  |  |  |  | 340 |  |  |  |  | 345 |  |

| ctt | ttg | gag | gac | aat | tac | gtg | aaa | cac | ttt | ggt | gac | ttg | gtt aaa aag | 1168 |
| Leu | Leu | Glu | Asp | Asn | Tyr | Val | Lys | His | Phe | Gly | Asp | Leu | Val Lys Lys |
|  | 350 |  |  |  |  | 355 |  |  |  |  | 360 |  |  |

| gct | aag | ccc | atc | cat | gga | gct | gat | gct | gtt | ttg | aaa | gca | ttt aac ata | 1216 |
| Ala | Lys | Pro | Ile | His | Gly | Ala | Asp | Ala | Val | Leu | Lys | Ala | Phe Asn Ile |
| 365 |  |  |  |  | 370 |  |  |  |  | 375 |  |  | 380 |

| gat | ggt | gat | gtg | cgt | att | cag | tac | aga | gat | caa | cta | gac | ttt gaa gat | 1264 |
| Asp | Gly | Asp | Val | Arg | Ile | Gln | Tyr | Arg | Asp | Gln | Leu | Asp | Phe Glu Asp |
|  |  |  |  | 385 |  |  |  |  | 390 |  |  |  | 395 |

| atc | gca | cgg | caa | ttt | ggc | att | ttt | gaa | gaa | tgg | aag | gat | ggt gta cca | 1312 |
| Ile | Ala | Arg | Gln | Phe | Gly | Ile | Phe | Glu | Glu | Trp | Lys | Asp | Gly Val Pro |
|  |  |  | 400 |  |  |  |  | 405 |  |  |  |  | 410 |

| cgg | gca | gca | tat | aaa | gga | ata | gtg | gtt | ttc | cgg | tac | caa | acg tcc aga | 1360 |
| Arg | Ala | Ala | Tyr | Lys | Gly | Ile | Val | Val | Phe | Arg | Tyr | Gln | Thr Ser Arg |
|  |  | 415 |  |  |  |  | 420 |  |  |  |  | 425 |  |

| cgt | gta | ttc | ctt | gtt | ggc | cct | gat | tcg | ctt | caa | caa | ctc | gga aat gaa | 1408 |
| Arg | Val | Phe | Leu | Val | Gly | Pro | Asp | Ser | Leu | Gln | Gln | Leu | Gly Asn Glu |
|  | 430 |  |  |  |  | 435 |  |  |  |  | 440 |  |  |

| gat | act | taa | caaagatatg | attggagccc | ggacaaagat | ttagacttat | 1457 |
| Asp | Thr |  |  |  |  |  |  |
| 445 |  |  |  |  |  |  |  | tgggtaggat gcatcgagct gacaccaaac catgagttta ccagttacat acaacgtttt   1517 aattgttata tggaggagct cactgttcta gtgttgaagg gatatcggct tcttaatatt   1577 ggatgaatca tcacaaccta tttttttaa gccaagtgtt ccgaacataa agaggaaatg   1637

-continued

```
tagccctgta aagacaatac ctgggacgat cataatcaca ggtcaatagt tttgcttctc    1697
agaaggaaca ttacaattgt gagcactccg cacgccctct tttggaagaa tatgagaact    1757
tttctcattt actctagtct attttggaaa tgcagattcc tcagaattta tattactctt    1817
agtgttgtca aattgacgaa cacaactgtg agcacgtaat ttttcccta caaaatactc    1877 ctacaaaaat tcacaaaaaa tggattttc tacttgtttt tgattttata gttttagga     1937 attccctttt aattgtttat ttgcattgta gttgcatttc ttgtgcatgt taaatatctt    1997
aaaatcatag aaaataccat aaaaaaaaaa aaaa                                2031
```

<210> SEQ ID NO 8
<211> LENGTH: 446
<212> TYPE: PRT
<213> ORGANISM: Nicotiana tabacum

<400> SEQUENCE: 8

```
Met Arg Gly Tyr Lys Phe Cys Cys Asp Phe Arg Tyr Leu Leu Ile Leu
1               5                   10                  15

Ala Ala Val Ala Phe Ile Tyr Ile Gln Met Arg Leu Phe Ala Thr Gln
            20                  25                  30

Ser Glu Tyr Ala Asp Arg Leu Ala Ala Ile Glu Ala Glu Asn His
        35                  40                  45

Cys Thr Ser Gln Thr Arg Leu Leu Ile Asp Gln Ile Ser Gln Gln Gln
50                  55                  60

Gly Arg Ile Val Ala Leu Glu Glu Gln Met Lys Arg Gln Asp Gln Glu
65                  70                  75                  80

Cys Arg Gln Leu Arg Ala Leu Val Gln Asp Leu Glu Ser Lys Gly Ile
                85                  90                  95

Lys Lys Leu Ile Gly Asn Val Gln Met Pro Val Ala Ala Val Val Val
            100                 105                 110

Met Ala Cys Asn Arg Ala Asp Tyr Leu Glu Lys Thr Ile Lys Ser Ile
        115                 120                 125

Leu Lys Tyr Gln Ile Ser Val Ala Pro Lys Tyr Pro Leu Phe Ile Ser
    130                 135                 140

Gln Asp Gly Ser His Pro Asp Val Arg Lys Leu Ala Leu Ser Tyr Asp
145                 150                 155                 160

Gln Leu Thr Tyr Met Gln His Leu Asp Phe Glu Pro Val His Thr Glu
                165                 170                 175

Arg Pro Gly Glu Leu Ile Ala Tyr Tyr Lys Ile Ala Arg His Tyr Lys
            180                 185                 190

Trp Ala Leu Asp Gln Leu Phe Tyr Lys His Asn Phe Ser Arg Val Ile
        195                 200                 205

Ile Leu Glu Asp Asp Met Glu Ile Ala Pro Asp Phe Phe Asp Phe Phe
    210                 215                 220

Glu Ala Gly Ala Thr Leu Leu Asp Arg Asp Lys Ser Ile Met Ala Ile
225                 230                 235                 240

Ser Ser Trp Asn Asp Asn Gly Gln Met Gln Phe Val Gln Asp Pro Tyr
                245                 250                 255

Ala Leu Tyr Arg Ser Asp Phe Phe Pro Gly Leu Gly Trp Met Leu Ser
            260                 265                 270

Lys Ser Thr Trp Asp Glu Leu Ser Pro Lys Trp Pro Lys Ala Tyr Trp
        275                 280                 285

Asp Asp Trp Leu Arg Leu Lys Glu Asn His Arg Gly Arg Gln Phe Ile
    290                 295                 300
```

-continued

```
Arg Pro Glu Val Cys Arg Ser Tyr Asn Phe Gly Glu His Gly Ser Ser
305                 310                 315                 320

Leu Gly Gln Phe Phe Lys Gln Tyr Leu Glu Pro Ile Lys Leu Asn Asp
            325                 330                 335

Val Gln Val Asp Trp Lys Ser Met Asp Leu Ser Tyr Leu Leu Glu Asp
        340                 345                 350

Asn Tyr Val Lys His Phe Gly Asp Leu Val Lys Ala Lys Pro Ile
    355                 360                 365

His Gly Ala Asp Ala Val Leu Lys Ala Phe Asn Ile Asp Gly Asp Val
370                 375                 380

Arg Ile Gln Tyr Arg Asp Gln Leu Asp Phe Glu Asp Ile Ala Arg Gln
385                 390                 395                 400

Phe Gly Ile Phe Glu Glu Trp Lys Asp Gly Val Pro Arg Ala Ala Tyr
            405                 410                 415

Lys Gly Ile Val Val Phe Arg Tyr Gln Thr Ser Arg Arg Val Phe Leu
        420                 425                 430

Val Gly Pro Asp Ser Leu Gln Gln Leu Gly Asn Glu Asp Thr
    435                 440                 445

<210> SEQ ID NO 9
<211> LENGTH: 1929
<212> TYPE: DNA
<213> ORGANISM: Oryza sativa
<220> FEATURE:
<221> NAME/KEY: CDS
<222> LOCATION: (15)..(1670)
<223> OTHER INFORMATION:

<400> SEQUENCE: 9
gcgatctccc ggcc atg gcg acg cgc cgg gcc ctc tcc tcc ctc gtc cgc        50
                Met Ala Thr Arg Arg Ala Leu Ser Ser Leu Val Arg
                1               5                   10 gcc gcc tcc agg ctc cgc ggg gcc tcg ccc gcc ccg cgc ccg cgc ggg        98
Ala Ala Ser Arg Leu Arg Gly Ala Ser Pro Ala Pro Arg Pro Arg Gly
            15                  20                  25 ccg ctc cac cga ccg tcg cca tcg ggg tac ctc ttc aac cgc gcc gcc       146
Pro Leu His Arg Pro Ser Pro Ser Gly Tyr Leu Phe Asn Arg Ala Ala
    30                  35                  40 gcg tac gcc acg gcc gcc gcg gcg aag gag cgg cct ccc gcg ccc gcg       194
Ala Tyr Ala Thr Ala Ala Ala Ala Lys Glu Arg Pro Ala Pro Ala
45                  50                  55                  60 acg ggg aag gcc acg ggt gga ggt aag atc acc gac gag ttc acc ggc       242
Thr Gly Lys Ala Thr Gly Gly Gly Lys Ile Thr Asp Glu Phe Thr Gly
                65                  70                  75 gcc ggc gcc att ggg cag gtg tgc cag gtc atc ggc gcc gtc gtc gac       290
Ala Gly Ala Ile Gly Gln Val Cys Gln Val Ile Gly Ala Val Val Asp
            80                  85                  90 gtg cgg ttt gac gag ggg ctg cct ccc atc ctc acg gcg ctc gag gtg       338
Val Arg Phe Asp Glu Gly Leu Pro Pro Ile Leu Thr Ala Leu Glu Val
        95                  100                 105 ctc gac cac aac atc cgc ctc gtg ctc gag gtg gcg cag cac ctt ggc       386
Leu Asp His Asn Ile Arg Leu Val Leu Glu Val Ala Gln His Leu Gly
    110                 115                 120 gag aac atg gtg cgc acc atc gct atg gac ggg act gag ggg ctt gtc       434
Glu Asn Met Val Arg Thr Ile Ala Met Asp Gly Thr Glu Gly Leu Val
125                 130                 135                 140 cgc ggt cag cgc gtc ctc aac acc ggc tcc cca atc act gtt cct gtt       482
Arg Gly Gln Arg Val Leu Asn Thr Gly Ser Pro Ile Thr Val Pro Val
                145                 150                 155
```

-continued

| | | |
|---|---|---|
| ggc agg gcc acg ctt gga cgt atc atg aat gtt att ggt gag cca att<br>Gly Arg Ala Thr Leu Gly Arg Ile Met Asn Val Ile Gly Glu Pro Ile<br>160                            165                     170 | 530 |
| gat gag aag ggt gac ata aca acg aac cac ttc ctt ccc atc cat cgt<br>Asp Glu Lys Gly Asp Ile Thr Thr Asn His Phe Leu Pro Ile His Arg<br>        175                        180                      185 | 578 |
| gag gcg cct gct ttt gtt gag caa gcc aca gaa cag caa att ctt gtt<br>Glu Ala Pro Ala Phe Val Glu Gln Ala Thr Glu Gln Gln Ile Leu Val<br>      190                        195                      200 | 626 |
| act gga att aag gtt gtg gat ctc gtt gcg ccc tac caa aga ggt gga<br>Thr Gly Ile Lys Val Val Asp Leu Val Ala Pro Tyr Gln Arg Gly Gly<br>205                          210                      215                  220 | 674 |
| aag atc ggt ctt ttt ggt ggt gca gga gtc ggc aaa act gtc ctt att<br>Lys Ile Gly Leu Phe Gly Gly Ala Gly Val Gly Lys Thr Val Leu Ile<br>                      225                      230                      235 | 722 |
| atg gag ttg atc aac aat gtt gct aag gcc cat ggt ggt ttc tct gtg<br>Met Glu Leu Ile Asn Asn Val Ala Lys Ala His Gly Gly Phe Ser Val<br>              240                      245                      250 | 770 |
| ttt gct ggt gtt ggt gaa cgt acc cgt gaa ggt aat gat ctt tac agg<br>Phe Ala Gly Val Gly Glu Arg Thr Arg Glu Gly Asn Asp Leu Tyr Arg<br>      255                        260                      265 | 818 |
| gaa atg att gaa agt ggt gtc atc aag cta ggt gac aaa cag agt gaa<br>Glu Met Ile Glu Ser Gly Val Ile Lys Leu Gly Asp Lys Gln Ser Glu<br>270                          275                      280 | 866 |
| agc aag tgt gct ctt gtc tac ggg caa atg aat gag ccc ccg ggt gct<br>Ser Lys Cys Ala Leu Val Tyr Gly Gln Met Asn Glu Pro Pro Gly Ala<br>285                          290                      295                  300 | 914 |
| cgt gct cgt gtt ggg ttg acc ggt ttg act gtt gcg gtt cat ttc cgt<br>Arg Ala Arg Val Gly Leu Thr Gly Leu Thr Val Ala Val His Phe Arg<br>                      305                      310                      315 | 962 |
| gat gcc gaa ggt caa gat gtg ctt ttg ttc att gac aac att ttt cgt<br>Asp Ala Glu Gly Gln Asp Val Leu Leu Phe Ile Asp Asn Ile Phe Arg<br>              320                      325                      330 | 1010 |
| ttc act cag gcg aac tct gag gtg tct gct ctt ctt gga cgt att cca<br>Phe Thr Gln Ala Asn Ser Glu Val Ser Ala Leu Leu Gly Arg Ile Pro<br>      335                        340                      345 | 1058 |
| tct gct gtg gga tat caa cca act ctt gct act gat ctt gga gga ctt<br>Ser Ala Val Gly Tyr Gln Pro Thr Leu Ala Thr Asp Leu Gly Gly Leu<br>350                          355                      360 | 1106 |
| caa gag cga att aca act aca aag aag ggt tcc att aca tct gtc caa<br>Gln Glu Arg Ile Thr Thr Thr Lys Lys Gly Ser Ile Thr Ser Val Gln<br>365                          370                      375                  380 | 1154 |
| gct att tat gtg cct gct gat gac ttg acg gat cct gct cct gct act<br>Ala Ile Tyr Val Pro Ala Asp Asp Leu Thr Asp Pro Ala Pro Ala Thr<br>                      385                      390                      395 | 1202 |
| act ttt gca cat ctt gat gct act act gtg ttg tca cga cag atc tct<br>Thr Phe Ala His Leu Asp Ala Thr Thr Val Leu Ser Arg Gln Ile Ser<br>              400                      405                      410 | 1250 |
| gag ctt ggt att tac cct gct gtc gat cct ctg gac tcc aca tcc aga<br>Glu Leu Gly Ile Tyr Pro Ala Val Asp Pro Leu Asp Ser Thr Ser Arg<br>      415                        420                      425 | 1298 |
| atg ctc tcc ccc cat gtt ttg ggt gag gat cac tac aac act gct cgt<br>Met Leu Ser Pro His Val Leu Gly Glu Asp His Tyr Asn Thr Ala Arg<br>430                          435                      440 | 1346 |
| ggt gtc caa agg gtt ctt cag aac tac aag aat ctt cag gat att att<br>Gly Val Gln Arg Val Leu Gln Asn Tyr Lys Asn Leu Gln Asp Ile Ile<br>445                          450                      455                  460 | 1394 |
| gca att ttg ggt atg gac gag ctc agt gaa gat gac agg ttg acc gtc<br>Ala Ile Leu Gly Met Asp Glu Leu Ser Glu Asp Asp Arg Leu Thr Val | 1442 |

```
                         465                 470                 475
cgt cgc gca agg aag atc cag cgt ttc ttg agc cag ccc ttc cat gtg    1490
Arg Arg Ala Arg Lys Ile Gln Arg Phe Leu Ser Gln Pro Phe His Val
            480                 485                 490 gct gaa gtt ttc acg ggt gct cct ggg aag tac gtg gag ctg aag gag    1538
Ala Glu Val Phe Thr Gly Ala Pro Gly Lys Tyr Val Glu Leu Lys Glu
        495                 500                 505 agc gtc aac agt ttc cag ggt gtt ttg gat ggg aaa tat gat gac ctt    1586
Ser Val Asn Ser Phe Gln Gly Val Leu Asp Gly Lys Tyr Asp Asp Leu
    510                 515                 520 ccc gag cag tca ttc tat atg gtg gga ggc att gag gaa gtc att gct    1634
Pro Glu Gln Ser Phe Tyr Met Val Gly Gly Ile Glu Glu Val Ile Ala
525                 530                 535                 540 aaa gct gag aag atc gcc aag gag tcg gct tca tag atctcttcat         1680
Lys Ala Glu Lys Ile Ala Lys Glu Ser Ala Ser
                545                 550 tgttgttaag ttctgtacaa gttaaatttt ggattctggc tttctatatg cccgttctgt  1740
agccaggacg tgattacaag caggggtgac atcttcagat gagcgatgtt ttttgtcttt  1800
ccttttctcc ttttacccct aataaggaac cgcagtgaca ttgtattgtg ctgcacaaaa  1860
gtactcggaa cttcgaaagc atgtgtcctt tataatgcag atccatgaag cataggatca  1920
aaaaaaaaa                                                          1929

<210> SEQ ID NO 10
<211> LENGTH: 551
<212> TYPE: PRT
<213> ORGANISM: Oryza sativa

<400> SEQUENCE: 10

Met Ala Thr Arg Arg Ala Leu Ser Ser Leu Val Arg Ala Ala Ser Arg
1               5                   10                  15

Leu Arg Gly Ala Ser Pro Ala Pro Arg Pro Arg Gly Pro Leu His Arg
            20                  25                  30

Pro Ser Pro Ser Gly Tyr Leu Phe Asn Arg Ala Ala Ala Tyr Ala Thr
        35                  40                  45

Ala Ala Ala Ala Lys Glu Arg Pro Ala Pro Ala Thr Gly Lys Ala
    50                  55                  60

Thr Gly Gly Gly Lys Ile Thr Asp Glu Phe Thr Gly Ala Gly Ala Ile
65                  70                  75                  80

Gly Gln Val Cys Gln Val Ile Gly Ala Val Val Asp Val Arg Phe Asp
                85                  90                  95

Glu Gly Leu Pro Pro Ile Leu Thr Ala Leu Glu Val Leu Asp His Asn
            100                 105                 110

Ile Arg Leu Val Leu Glu Val Ala Gln His Leu Gly Glu Asn Met Val
        115                 120                 125

Arg Thr Ile Ala Met Asp Gly Thr Glu Gly Leu Val Arg Gly Gln Arg
    130                 135                 140

Val Leu Asn Thr Gly Ser Pro Ile Thr Val Pro Val Gly Arg Ala Thr
145                 150                 155                 160

Leu Gly Arg Ile Met Asn Val Ile Gly Glu Pro Ile Asp Glu Lys Gly
                165                 170                 175

Asp Ile Thr Thr Asn His Phe Leu Pro Ile His Arg Glu Ala Pro Ala
            180                 185                 190

Phe Val Glu Gln Ala Thr Glu Gln Gln Ile Leu Val Thr Gly Ile Lys
        195                 200                 205
```

```
Val Val Asp Leu Val Ala Pro Tyr Gln Arg Gly Gly Lys Ile Gly Leu
    210                 215                 220

Phe Gly Gly Ala Gly Val Gly Lys Thr Val Leu Ile Met Glu Leu Ile
225                 230                 235                 240

Asn Asn Val Ala Lys Ala His Gly Gly Phe Ser Val Phe Ala Gly Val
                245                 250                 255

Gly Glu Arg Thr Arg Glu Gly Asn Asp Leu Tyr Arg Glu Met Ile Glu
            260                 265                 270

Ser Gly Val Ile Lys Leu Gly Asp Lys Gln Ser Glu Ser Lys Cys Ala
                275                 280                 285

Leu Val Tyr Gly Gln Met Asn Glu Pro Pro Gly Ala Arg Ala Arg Val
    290                 295                 300

Gly Leu Thr Gly Leu Thr Val Ala Val His Phe Arg Asp Ala Glu Gly
305                 310                 315                 320

Gln Asp Val Leu Leu Phe Ile Asp Asn Ile Phe Arg Phe Thr Gln Ala
                325                 330                 335

Asn Ser Glu Val Ser Ala Leu Leu Gly Arg Ile Pro Ser Ala Val Gly
            340                 345                 350

Tyr Gln Pro Thr Leu Ala Thr Asp Leu Gly Gly Leu Gln Glu Arg Ile
                355                 360                 365

Thr Thr Thr Lys Lys Gly Ser Ile Thr Ser Val Gln Ala Ile Tyr Val
370                 375                 380

Pro Ala Asp Asp Leu Thr Asp Pro Ala Pro Ala Thr Thr Phe Ala His
385                 390                 395                 400

Leu Asp Ala Thr Thr Val Leu Ser Arg Gln Ile Ser Glu Leu Gly Ile
                405                 410                 415

Tyr Pro Ala Val Asp Pro Leu Asp Ser Thr Ser Arg Met Leu Ser Pro
                420                 425                 430

His Val Leu Gly Glu Asp His Tyr Asn Thr Ala Arg Gly Val Gln Arg
            435                 440                 445

Val Leu Gln Asn Tyr Lys Asn Leu Gln Asp Ile Ile Ala Ile Leu Gly
    450                 455                 460

Met Asp Glu Leu Ser Glu Asp Arg Leu Thr Val Arg Arg Ala Arg
465                 470                 475                 480

Lys Ile Gln Arg Phe Leu Ser Gln Pro Phe His Val Ala Glu Val Phe
                485                 490                 495

Thr Gly Ala Pro Gly Lys Tyr Val Glu Leu Lys Glu Ser Val Asn Ser
            500                 505                 510

Phe Gln Gly Val Leu Asp Gly Lys Tyr Asp Asp Leu Pro Glu Gln Ser
    515                 520                 525

Phe Tyr Met Val Gly Gly Ile Glu Glu Val Ile Ala Lys Ala Glu Lys
    530                 535                 540

Ile Ala Lys Glu Ser Ala Ser
545                 550

<210> SEQ ID NO 11
<211> LENGTH: 1267
<212> TYPE: DNA
<213> ORGANISM: Arabidopsis sp.
<220> FEATURE:
<221> NAME/KEY: CDS
<222> LOCATION: (75)..(1052)
<223> OTHER INFORMATION:

<400> SEQUENCE: 11
tctctctcta taatccgatc tgagaaattt cgccggagct aggttttgtt gtttaccgat     60
```

-continued

```
caatccttta atca atg gca atg gct gtt ttc cgt cgc gaa ggg agg cgt      110
              Met Ala Met Ala Val Phe Arg Arg Glu Gly Arg Arg
              1             5                   10 ctc ctc cct tca atc gcc gct cgc cca atc gct gct atc cga tct cct      158
Leu Leu Pro Ser Ile Ala Ala Arg Pro Ile Ala Ala Ile Arg Ser Pro
        15                  20                  25 ctc tct tct gac cag gag gaa gga ctt ctt gga gtt cga tct atc tca      206
Leu Ser Ser Asp Gln Glu Glu Gly Leu Leu Gly Val Arg Ser Ile Ser
    30                  35                  40 act caa gtg gtg cgt aac cgc atg aag agt gtt aag aac atc caa aag      254
Thr Gln Val Val Arg Asn Arg Met Lys Ser Val Lys Asn Ile Gln Lys
45                  50                  55                  60 atc aca aag gca atg aag atg gtt gct gct tcc aag ctt aga gca gtt      302
Ile Thr Lys Ala Met Lys Met Val Ala Ala Ser Lys Leu Arg Ala Val
                65                  70                  75 cag ggc cga gct gag aac tcc cgt gga ctt tgg cag cca ttt act gca      350
Gln Gly Arg Ala Glu Asn Ser Arg Gly Leu Trp Gln Pro Phe Thr Ala
            80                  85                  90 ctt cta gga gat aat ccc agc att gat gta aag aag agt gtg gtg gtc      398
Leu Leu Gly Asp Asn Pro Ser Ile Asp Val Lys Lys Ser Val Val Val
        95                  100                 105 act ctc tct tct gac aag ggt ctc tgt ggt gga atc aac tcc act gtc      446
Thr Leu Ser Ser Asp Lys Gly Leu Cys Gly Gly Ile Asn Ser Thr Val
    110                 115                 120 gtt aaa gtg agc agg gct ctg tac aaa ttg aat gct ggt cct gaa aag      494
Val Lys Val Ser Arg Ala Leu Tyr Lys Leu Asn Ala Gly Pro Glu Lys
125                 130                 135                 140 gaa gtt cag ttt gtt att gtc gga gag aaa gca aag gct ata atg ttt      542
Glu Val Gln Phe Val Ile Val Gly Glu Lys Ala Lys Ala Ile Met Phe
                145                 150                 155 cgt gac tca aaa aac gac att gtc ctc tct gta aca gag ctg aat aag      590
Arg Asp Ser Lys Asn Asp Ile Val Leu Ser Val Thr Glu Leu Asn Lys
            160                 165                 170 aac cca ctc aat tat gct cag gtg tca gtt cta gct gat gac atc ctg      638
Asn Pro Leu Asn Tyr Ala Gln Val Ser Val Leu Ala Asp Asp Ile Leu
        175                 180                 185 aag aac gtt gaa ttt gat gct ttg cgc att gtc tac aac aag ttc cat      686
Lys Asn Val Glu Phe Asp Ala Leu Arg Ile Val Tyr Asn Lys Phe His
    190                 195                 200 tca gtt gtc gca ttt ctg cca act gtg tcc act gtt ttg tca cct gag      734
Ser Val Val Ala Phe Leu Pro Thr Val Ser Thr Val Leu Ser Pro Glu
205                 210                 215                 220 att att gag aag gag tct gaa att gga gga aaa ctt ggc gag ctt gac      782
Ile Ile Glu Lys Glu Ser Glu Ile Gly Gly Lys Leu Gly Glu Leu Asp
                225                 230                 235 tca tat gag att gag ggt ggg gaa aca aag gga gaa ata ttg cag aat      830
Ser Tyr Glu Ile Glu Gly Gly Glu Thr Lys Gly Glu Ile Leu Gln Asn
            240                 245                 250 ctg gcc gag ttc caa ttc tct tgt gtg atg ttc aat gcg gtt ctg gag      878
Leu Ala Glu Phe Gln Phe Ser Cys Val Met Phe Asn Ala Val Leu Glu
        255                 260                 265 aat gca tgt agt gag atg gga gca aga atg tct gcc atg gac agc tca      926
Asn Ala Cys Ser Glu Met Gly Ala Arg Met Ser Ala Met Asp Ser Ser
    270                 275                 280 agc aga aac gca gga gaa atg ctc gac cgt ctc acc ctc aca tac aac      974
Ser Arg Asn Ala Gly Glu Met Leu Asp Arg Leu Thr Leu Thr Tyr Asn
285                 290                 295                 300 agg act cgt caa gct tct att aca aca gag ctt att gag att atc tct     1022
Arg Thr Arg Gln Ala Ser Ile Thr Thr Glu Leu Ile Glu Ile Ile Ser
```

```
                  305                 310                 315
gga gct tct gct ctt gaa gct gct aaa taa gcccatccgt gttagttctc      1072
Gly Ala Ser Ala Leu Glu Ala Ala Lys
            320                 325 tttcttcgc tttgatattt accccccacct tgaaggagaa gagtgtgtta aaattttact   1132
gaatcagttt cctttgctgg cttcttgttg agacctacca atgtttgctc aacgattttt   1192
aataaacata cctgtaattt ccagcaggat ttcgaataat tgcattaaca ttttgttctg   1252
aaaaaaaaaa aaaaa                                                    1267
```

<210> SEQ ID NO 12
<211> LENGTH: 325
<212> TYPE: PRT
<213> ORGANISM: Arabidopsis sp.

<400> SEQUENCE: 12

```
Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Met Lys Ser Val Lys Asn Ile Gln Lys Ile Thr Lys Ala
    50                  55                  60

Met Lys Met Val Ala Ala Ser Lys Leu Arg Ala Val Gln Gly Arg Ala
65                  70                  75                  80

Glu Asn Ser Arg Gly Leu Trp Gln Pro Phe Thr Ala Leu Leu Gly Asp
                85                  90                  95

Asn Pro Ser Ile Asp Val Lys Lys Ser Val Val Val Thr Leu Ser Ser
            100                 105                 110

Asp Lys Gly Leu Cys Gly Gly Ile Asn Ser Thr Val Val Lys Val Ser
        115                 120                 125

Arg Ala Leu Tyr Lys Leu Asn Ala Gly Pro Glu Lys Glu Val Gln Phe
    130                 135                 140

Val Ile Val Gly Glu Lys Ala Lys Ala Ile Met Phe Arg Asp Ser Lys
145                 150                 155                 160

Asn Asp Ile Val Leu Ser Val Thr Glu Leu Asn Lys Asn Pro Leu Asn
                165                 170                 175

Tyr Ala Gln Val Ser Val Leu Ala Asp Asp Ile Leu Lys Asn Val Glu
            180                 185                 190

Phe Asp Ala Leu Arg Ile Val Tyr Asn Lys Phe His Ser Val Val Ala
        195                 200                 205

Phe Leu Pro Thr Val Ser Thr Val Leu Ser Pro Glu Ile Ile Glu Lys
    210                 215                 220

Glu Ser Glu Ile Gly Gly Lys Leu Gly Glu Leu Asp Ser Tyr Glu Ile
225                 230                 235                 240

Glu Gly Gly Glu Thr Lys Gly Glu Ile Leu Gln Asn Leu Ala Glu Phe
                245                 250                 255

Gln Phe Ser Cys Val Met Phe Asn Ala Val Leu Glu Asn Ala Cys Ser
            260                 265                 270

Glu Met Gly Ala Arg Met Ser Ala Met Asp Ser Ser Arg Asn Ala
        275                 280                 285

Gly Glu Met Leu Asp Arg Leu Thr Leu Thr Tyr Asn Arg Thr Arg Gln
    290                 295                 300
```

-continued

```
Ala Ser Ile Thr Thr Glu Leu Ile Glu Ile Ile Ser Gly Ala Ser Ala
305                 310                 315                 320
Leu Glu Ala Ala Lys
            325
```